US012758219B2

(12) United States Patent
Nicholas

(10) Patent No.: US 12,758,219 B2
(45) Date of Patent: *Oct. 13, 2026

(54) SURGICAL SYSTEM INCLUDING ADAPTER ASSEMBLY WITH WORM GEAR ASSEMBLY

(71) Applicant: Covidien LP, Mansfield, MA (US)

(72) Inventor: David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/191,704

(22) Filed: Apr. 28, 2025

(65) Prior Publication Data

US 2025/0248706 A1 Aug. 7, 2025

Related U.S. Application Data

(63) Continuation of application No. 18/407,343, filed on Jan. 8, 2024, now Pat. No. 12,303,128, which is a (Continued)

(51) Int. Cl.
*A61B 17/072* (2006.01)
*A61B 17/00* (2006.01)
(Continued)

(52) U.S. Cl.
CPC ........ *A61B 17/07207* (2013.01); *A61B 34/71* (2016.02); *A61B 2017/00398* (2013.01); (Continued)

(58) Field of Classification Search
CPC .............. A61B 17/07207; A61B 34/71; A61B 2034/715; A61B 2017/00398; (Continued)

(56) References Cited

U.S. PATENT DOCUMENTS

| | | | |
|---|---|---|---|
| 2,777,340 | A | 1/1957 | Hettwer et al. |
| 2,957,353 | A | 10/1960 | Babacz |

(Continued)

FOREIGN PATENT DOCUMENTS

| | | | |
|---|---|---|---|
| CA | 2451558 | A1 | 1/2003 |
| CA | 2824590 | A1 | 4/2014 |

(Continued)

OTHER PUBLICATIONS

Chinese Office Action dated Sep. 30, 2020 for application No. 2017103218172 with English Translation.

(Continued)

*Primary Examiner* — Dariush Seif

(57) ABSTRACT

A surgical system includes an end effector, a handle assembly that operates the end effector, and an adapter assembly that connects the end effector to the handle assembly. The adapter assembly includes an adapter housing, an outer tube, at least one gear assembly, and a worm gear assembly. The adapter housing has a proximal end portion connected to a distal end portion of the handle assembly. The outer tube extends distally from the adapter housing and supports the end effector on a distal end portion of the outer tube. The worm gear assembly is engaged with the at least one gear assembly and rotatable with the at least one gear assembly in the adapter housing to operate the end effector.

20 Claims, 11 Drawing Sheets

Related U.S. Application Data continuation of application No. 17/987,990, filed on Nov. 16, 2022, now Pat. No. 11,864,763, which is a continuation of application No. 17/034,490, filed on Sep. 28, 2020, now Pat. No. 11,504,123, which is a continuation of application No. 15/491,268, filed on Apr. 19, 2017, now Pat. No. 10,799,239.

(60) Provisional application No. 62/333,584, filed on May 9, 2016.

(51) Int. Cl.
*A61B 17/29* (2006.01)
*A61B 34/00* (2016.01)

(52) U.S. Cl.
CPC ................ *A61B 2017/0046* (2013.01); *A61B 2017/00473* (2013.01); *A61B 2017/07285* (2013.01); *A61B 2017/2927* (2013.01); *A61B 2034/715* (2016.02)

(58) Field of Classification Search
CPC .. A61B 2017/0046; A61B 2017/00473; A61B 2017/07285; A61B 2017/2927
USPC ...... 227/175.1–182.1; 606/75, 151, 219, 220
See application file for complete search history.

(56) References Cited

U.S. PATENT DOCUMENTS

| | | | | |
|---|---|---|---|---|
| 3,006,885 | A | | 10/1961 | Dickson, Jr. |
| 3,025,199 | A | | 3/1962 | Harwood |
| 3,111,328 | A | | 11/1963 | Di Rito et al. |
| 3,695,058 | A | | 10/1972 | Keith, Jr. |
| 3,734,515 | A | | 5/1973 | Dudek |
| 3,759,336 | A | | 9/1973 | Marcovitz et al. |
| 4,162,399 | A | | 7/1979 | Hudson |
| 4,544,090 | A | * | 10/1985 | Warman .................... B25C 1/06 227/134 |
| 4,606,343 | A | | 8/1986 | Conta et al. |
| 4,705,038 | A | | 11/1987 | Sjostrom et al. |
| 4,722,685 | A | | 2/1988 | De Estrada |
| 4,823,807 | A | | 4/1989 | Russell et al. |
| 4,874,181 | A | | 10/1989 | Hsu |
| 5,129,118 | A | | 7/1992 | Walmesley |
| 5,129,570 | A | | 7/1992 | Schulze et al. |
| 5,152,744 | A | | 10/1992 | Krause et al. |
| 5,301,061 | A | | 4/1994 | Nakada et al. |
| 5,312,023 | A | * | 5/1994 | Green ............. A61B 17/07207 227/19 |
| 5,326,013 | A | | 7/1994 | Green et al. |
| 5,350,355 | A | | 9/1994 | Sklar |
| 5,383,874 | A | | 1/1995 | Jackson et al. |
| 5,383,880 | A | | 1/1995 | Hooven |
| 5,389,098 | A | | 2/1995 | Tsuruta et al. |
| 5,395,033 | A | | 3/1995 | Byrne et al. |
| 5,400,267 | A | | 3/1995 | Denen et al. |
| 5,411,508 | A | | 5/1995 | Bessler et al. |
| 5,413,267 | A | | 5/1995 | Solyntjes et al. |
| 5,427,087 | A | | 6/1995 | Ito et al. |
| 5,433,721 | A | | 7/1995 | Hooven et al. |
| 5,467,911 | A | * | 11/1995 | Tsuruta ............. A61B 17/0684 227/19 |
| 5,476,379 | A | | 12/1995 | Disel |
| 5,487,499 | A | | 1/1996 | Sorrentino et al. |
| 5,518,163 | A | | 5/1996 | Hooven |
| 5,518,164 | A | | 5/1996 | Hooven |
| 5,526,822 | A | | 6/1996 | Burbank et al. |
| 5,529,235 | A | | 6/1996 | Boiarski et al. |
| 5,535,934 | A | | 7/1996 | Boiarski et al. |
| 5,535,937 | A | | 7/1996 | Boiarski et al. |
| 5,540,375 | A | | 7/1996 | Bolanos et al. |
| 5,540,706 | A | | 7/1996 | Aust et al. |
| 5,542,594 | A | | 8/1996 | Mckean et al. |
| 5,549,637 | A | | 8/1996 | Crainich |
| 5,553,675 | A | | 9/1996 | Pitzen et al. |
| 5,562,239 | A | | 10/1996 | Boiarski et al. |
| 5,564,615 | A | | 10/1996 | Bishop et al. |
| 5,582,617 | A | * | 12/1996 | Klieman ................ A61B 34/71 606/174 |
| 5,609,560 | A | | 3/1997 | Ichikawa et al. |
| 5,626,587 | A | | 5/1997 | Bishop et al. |
| 5,632,432 | A | | 5/1997 | Schulze et al. |
| 5,645,209 | A | | 7/1997 | Green et al. |
| 5,647,526 | A | | 7/1997 | Green et al. |
| 5,653,374 | A | | 8/1997 | Young et al. |
| 5,658,300 | A | | 8/1997 | Bito et al. |
| 5,662,662 | A | | 9/1997 | Bishop et al. |
| 5,667,517 | A | | 9/1997 | Hooven |
| 5,693,042 | A | | 12/1997 | Boiarski et al. |
| 5,704,534 | A | | 1/1998 | Huitema et al. |
| 5,711,472 | A | * | 1/1998 | Bryan .............. A61B 17/07207 227/19 |
| 5,713,505 | A | | 2/1998 | Huitema |
| 5,762,603 | A | | 6/1998 | Thompson |
| 5,779,130 | A | | 7/1998 | Alesi et al. |
| 5,782,396 | A | | 7/1998 | Mastri et al. |
| 5,782,397 | A | | 7/1998 | Koukline |
| 5,792,135 | A | | 8/1998 | Madhani et al. |
| 5,792,573 | A | | 8/1998 | Pitzen et al. |
| 5,797,536 | A | | 8/1998 | Smith et al. |
| 5,820,009 | A | | 10/1998 | Melling et al. |
| 5,863,159 | A | | 1/1999 | Lasko |
| 5,908,427 | A | | 6/1999 | Mckean et al. |
| 5,954,259 | A | | 9/1999 | Viola et al. |
| 5,964,774 | A | | 10/1999 | Mckean et al. |
| 5,993,454 | A | | 11/1999 | Longo |
| 6,010,054 | A | | 1/2000 | Johnson et al. |
| 6,017,354 | A | | 1/2000 | Culp et al. |
| 6,032,849 | A | | 3/2000 | Mastri et al. |
| 6,045,560 | A | | 4/2000 | Mckean et al. |
| 6,080,185 | A | * | 6/2000 | Johnson ............. A61B 17/8872 606/103 |
| 6,090,123 | A | | 7/2000 | Culp et al. |
| 6,126,651 | A | | 10/2000 | Mayer |
| 6,129,547 | A | | 10/2000 | Cise et al. |
| 6,165,169 | A | | 12/2000 | Panescu et al. |
| 6,239,732 | B1 | | 5/2001 | Cusey |
| 6,241,139 | B1 | | 6/2001 | Milliman et al. |
| 6,250,532 | B1 | * | 6/2001 | Green .............. A61B 17/07207 227/19 |
| 6,264,086 | B1 | | 7/2001 | Mcguckin, Jr. |
| 6,264,087 | B1 | | 7/2001 | Whitman |
| 6,302,311 | B1 | | 10/2001 | Adams et al. |
| 6,315,184 | B1 | | 11/2001 | Whitman |
| 6,321,855 | B1 | | 11/2001 | Barnes |
| 6,329,778 | B1 | | 12/2001 | Culp et al. |
| 6,343,731 | B1 | | 2/2002 | Adams et al. |
| 6,348,061 | B1 | | 2/2002 | Whitman |
| 6,368,324 | B1 | | 4/2002 | Dinger et al. |
| 6,371,909 | B1 | | 4/2002 | Hoeg et al. |
| 6,434,507 | B1 | | 8/2002 | Clayton et al. |
| 6,443,973 | B1 | | 9/2002 | Whitman |
| 6,461,372 | B1 | | 10/2002 | Jensen et al. |
| 6,488,197 | B1 | | 12/2002 | Whitman |
| 6,491,201 | B1 | | 12/2002 | Whitman |
| 6,533,157 | B1 | | 3/2003 | Whitman |
| 6,537,280 | B2 | | 3/2003 | Dinger et al. |
| 6,610,066 | B2 | | 8/2003 | Dinger et al. |
| 6,611,793 | B1 | | 8/2003 | Burnside et al. |
| 6,645,218 | B1 | | 11/2003 | Cassidy et al. |
| 6,654,999 | B2 | | 12/2003 | Stoddard et al. |
| 6,698,643 | B2 | | 3/2004 | Whitman |
| 6,699,177 | B1 | | 3/2004 | Wang et al. |
| 6,716,233 | B1 | | 4/2004 | Whitman |
| 6,743,240 | B2 | | 6/2004 | Smith et al. |
| 6,783,533 | B2 | | 8/2004 | Green et al. |
| 6,792,390 | B1 | | 9/2004 | Burnside et al. |
| 6,793,652 | B1 | | 9/2004 | Whitman et al. |
| 6,817,508 | B1 | | 11/2004 | Racenet et al. |
| 6,830,174 | B2 | | 12/2004 | Hillstead et al. |
| 6,846,308 | B2 | | 1/2005 | Whitman et al. |
| 6,846,309 | B2 | | 1/2005 | Whitman et al. |

(56) References Cited

U.S. PATENT DOCUMENTS

| | | | |
|---|---|---|---|
| 6,849,071 | B2 | 2/2005 | Whitman et al. |
| 6,860,892 | B1 | 3/2005 | Tanaka et al. |
| 6,899,538 | B2 | 5/2005 | Matoba |
| 6,905,057 | B2 | 6/2005 | Swayze et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 6,981,941 | B2 | 1/2006 | Whitman et al. |
| 6,986,451 | B1 | 1/2006 | Mastri et al. |
| 6,988,649 | B2 | 1/2006 | Shelton, IV et al. |
| 7,032,798 | B2 | 4/2006 | Whitman et al. |
| RE39,152 | E | 6/2006 | Aust et al. |
| 7,055,731 | B2 | 6/2006 | Shelton, IV et al. |
| 7,059,508 | B2 | 6/2006 | Shelton, IV et al. |
| 7,077,856 | B2 | 7/2006 | Whitman |
| 7,111,769 | B2 | 9/2006 | Wales et al. |
| 7,122,029 | B2 | 10/2006 | Koop et al. |
| 7,140,528 | B2 | 11/2006 | Shelton, IV |
| 7,141,049 | B2 | 11/2006 | Stern et al. |
| 7,143,923 | B2 | 12/2006 | Shelton, IV et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,172,104 | B2 | 2/2007 | Scirica et al. |
| 7,225,964 | B2 | 6/2007 | Mastri et al. |
| 7,238,021 | B1 | 7/2007 | Johnson |
| 7,246,734 | B2 | 7/2007 | Shelton, IV |
| 7,252,660 | B2 | 8/2007 | Kunz |
| 7,328,828 | B2 | 2/2008 | Ortiz et al. |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,422,139 | B2 | 9/2008 | Shelton, IV et al. |
| 7,431,189 | B2 | 10/2008 | Shelton, IV et al. |
| 7,441,684 | B2 | 10/2008 | Shelton, IV et al. |
| 7,448,525 | B2 | 11/2008 | Shelton, IV et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,481,347 | B2 | 1/2009 | Roy |
| 7,481,824 | B2 | 1/2009 | Boudreaux et al. |
| 7,487,899 | B2 | 2/2009 | Shelton, IV et al. |
| 7,549,564 | B2 | 6/2009 | Boudreaux |
| 7,565,993 | B2 | 7/2009 | Milliman et al. |
| 7,568,603 | B2 | 8/2009 | Shelton, IV et al. |
| 7,575,144 | B2 | 8/2009 | Ortiz et al. |
| 7,588,175 | B2 | 9/2009 | Timm et al. |
| 7,588,176 | B2 | 9/2009 | Timm et al. |
| 7,637,409 | B2 | 12/2009 | Marczyk |
| 7,641,093 | B2 | 1/2010 | Doll et al. |
| 7,644,848 | B2 | 1/2010 | Swayze et al. |
| 7,670,334 | B2 | 3/2010 | Hueil et al. |
| 7,673,780 | B2 | 3/2010 | Shelton, IV et al. |
| 7,699,835 | B2 | 4/2010 | Lee et al. |
| 7,721,931 | B2 | 5/2010 | Shelton, IV et al. |
| 7,738,971 | B2 | 6/2010 | Swayze et al. |
| 7,740,159 | B2 | 6/2010 | Shelton, IV et al. |
| 7,743,960 | B2 | 6/2010 | Whitman et al. |
| 7,758,613 | B2 | 7/2010 | Whitman |
| 7,766,210 | B2 | 8/2010 | Shelton, IV et al. |
| 7,770,773 | B2 | 8/2010 | Whitman et al. |
| 7,770,775 | B2 | 8/2010 | Shelton, IV et al. |
| 7,793,812 | B2 | 9/2010 | Moore et al. |
| 7,799,039 | B2 | 9/2010 | Shelton, IV et al. |
| 7,802,712 | B2 | 9/2010 | Milliman et al. |
| 7,803,151 | B2 | 9/2010 | Whitman |
| 7,822,458 | B2 | 10/2010 | Webster, III et al. |
| 7,845,534 | B2 | 12/2010 | Viola et al. |
| 7,845,537 | B2 | 12/2010 | Shelton, IV et al. |
| 7,857,185 | B2 | 12/2010 | Swayze et al. |
| 7,870,989 | B2 | 1/2011 | Viola et al. |
| 7,900,805 | B2 | 3/2011 | Shelton, IV et al. |
| 7,905,897 | B2 | 3/2011 | Whitman et al. |
| 7,918,230 | B2 | 4/2011 | Whitman et al. |
| 7,922,061 | B2 | 4/2011 | Shelton, IV et al. |
| 7,922,719 | B2 | 4/2011 | Ralph et al. |
| 7,947,034 | B2 | 5/2011 | Whitman |
| 7,951,071 | B2 | 5/2011 | Whitman et al. |
| 7,954,682 | B2 | 6/2011 | Giordano et al. |
| 7,959,051 | B2 | 6/2011 | Smith et al. |
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,992,758 | B2 | 8/2011 | Whitman et al. |
| 8,006,885 | B2 * | 8/2011 | Marczyk .......... A61B 17/07207 227/176.1 |
| 8,011,550 | B2 | 9/2011 | Aranyi et al. |
| 8,016,178 | B2 | 9/2011 | Olson et al. |
| 8,016,855 | B2 | 9/2011 | Whitman et al. |
| 8,020,743 | B2 | 9/2011 | Shelton, IV |
| 8,025,199 | B2 | 9/2011 | Whitman et al. |
| 8,035,487 | B2 | 10/2011 | Malackowski |
| 8,052,024 | B2 | 11/2011 | Viola et al. |
| 8,114,118 | B2 | 2/2012 | Knodel et al. |
| 8,127,975 | B2 | 3/2012 | Olson et al. |
| 8,132,705 | B2 | 3/2012 | Viola et al. |
| 8,152,516 | B2 | 4/2012 | Harvey et al. |
| 8,157,150 | B2 | 4/2012 | Viola et al. |
| 8,157,151 | B2 | 4/2012 | Ingmanson et al. |
| 8,182,494 | B1 | 5/2012 | Yencho et al. |
| 8,186,555 | B2 | 5/2012 | Shelton, IV et al. |
| 8,186,587 | B2 | 5/2012 | Zmood et al. |
| 8,220,367 | B2 | 7/2012 | Hsu |
| 8,235,273 | B2 | 8/2012 | Olson et al. |
| 8,241,322 | B2 | 8/2012 | Whitman et al. |
| 8,272,554 | B2 | 9/2012 | Whitman et al. |
| 8,292,150 | B2 | 10/2012 | Bryant |
| 8,292,888 | B2 | 10/2012 | Whitman |
| 8,342,379 | B2 | 1/2013 | Whitman et al. |
| 8,348,130 | B2 | 1/2013 | Shah et al. |
| 8,348,855 | B2 | 1/2013 | Hillely et al. |
| 8,353,440 | B2 | 1/2013 | Whitman et al. |
| 8,357,144 | B2 | 1/2013 | Whitman et al. |
| 8,365,633 | B2 | 2/2013 | Simaan et al. |
| 8,365,972 | B2 | 2/2013 | Aranyi et al. |
| 8,371,492 | B2 | 2/2013 | Aranyi et al. |
| 8,372,057 | B2 | 2/2013 | Cude et al. |
| 8,391,957 | B2 | 3/2013 | Carlson et al. |
| 8,403,926 | B2 | 3/2013 | Nobis et al. |
| 8,418,904 | B2 | 4/2013 | Wenchell et al. |
| 8,424,739 | B2 | 4/2013 | Racenet et al. |
| 8,454,585 | B2 | 6/2013 | Whitman |
| 8,505,802 | B2 | 8/2013 | Viola et al. |
| 8,517,241 | B2 | 8/2013 | Nicholas et al. |
| 8,523,043 | B2 | 9/2013 | Ullrich et al. |
| 8,551,076 | B2 | 10/2013 | Duval et al. |
| 8,556,152 | B2 * | 10/2013 | Marczyk .............. A61B 17/068 227/19 |
| 8,561,871 | B2 | 10/2013 | Rajappa et al. |
| 8,561,874 | B2 | 10/2013 | Scirica |
| 8,602,287 | B2 | 12/2013 | Yates et al. |
| 8,623,000 | B2 | 1/2014 | Humayun et al. |
| 8,627,995 | B2 | 1/2014 | Smith et al. |
| 8,632,463 | B2 | 1/2014 | Drinan et al. |
| 8,636,766 | B2 | 1/2014 | Milliman et al. |
| 8,647,258 | B2 | 2/2014 | Aranyi et al. |
| 8,652,121 | B2 | 2/2014 | Quick et al. |
| 8,657,174 | B2 | 2/2014 | Yates et al. |
| 8,657,177 | B2 | 2/2014 | Scirica et al. |
| 8,672,206 | B2 | 3/2014 | Aranyi et al. |
| 8,696,552 | B2 | 4/2014 | Whitman |
| 8,708,213 | B2 | 4/2014 | Shelton, IV et al. |
| 8,715,306 | B2 | 5/2014 | Faller et al. |
| 8,758,391 | B2 | 6/2014 | Swayze et al. |
| 8,806,973 | B2 | 8/2014 | Ross et al. |
| 8,808,311 | B2 | 8/2014 | Heinrich et al. |
| 8,820,605 | B2 | 9/2014 | Shelton, IV |
| 8,851,355 | B2 | 10/2014 | Aranyi et al. |
| 8,858,571 | B2 | 10/2014 | Shelton, IV et al. |
| 8,875,972 | B2 | 11/2014 | Weisenburgh et al. |

(56) References Cited

U.S. PATENT DOCUMENTS 8,888,762 B2 11/2014 Whitman
8,893,946 B2 11/2014 Boudreaux et al.
8,899,462 B2 12/2014 Kostrzewski et al.
8,905,289 B2 12/2014 Patel et al.
8,919,630 B2 12/2014 Milliman
8,931,680 B2 1/2015 Milliman
8,939,344 B2 1/2015 Olson et al.
8,950,646 B2 2/2015 Viola
8,960,519 B2 2/2015 Whitman et al.
8,961,396 B2 2/2015 Azarbarzin et al.
8,967,443 B2 3/2015 Mccuen
8,968,276 B2 3/2015 Zemlok et al.
8,968,337 B2 3/2015 Whitfield et al.
8,992,422 B2 3/2015 Spivey et al.
9,016,545 B2 4/2015 Aranyi et al.
9,023,014 B2 5/2015 Chowaniec et al.
9,033,868 B2 5/2015 Whitman et al.
9,050,119 B2 6/2015 Devengenzo et al.
9,055,943 B2 6/2015 Zemlok et al.
9,064,653 B2 6/2015 Prest et al.
9,072,515 B2 7/2015 Hall et al.
9,113,847 B2 8/2015 Whitman et al.
9,113,875 B2 8/2015 Viola et al.
9,113,876 B2 8/2015 Zemlok et al.
9,113,899 B2 8/2015 Garrison et al.
9,216,013 B2 12/2015 Scirica et al.
9,271,799 B2 3/2016 Shelton, IV et al.
9,282,961 B2 3/2016 Whitman et al.
9,282,963 B2 3/2016 Bryant
9,295,522 B2 3/2016 Kostrzewski
9,307,986 B2 4/2016 Hall et al.
9,889,568 B2 2/2018 Kilroy et al.
10,258,333 B2 * 4/2019 Shelton, IV ..... A61B 17/07207
10,265,118 B2 4/2019 Gerhardt
10,799,239 B2 * 10/2020 Nicholas ................ A61B 34/71
11,504,123 B2 * 11/2022 Nicholas .......... A61B 17/07207
11,864,763 B2 * 1/2024 Nicholas ................ A61B 34/71
12,303,128 B2 * 5/2025 Nicholas .......... A61B 17/07207
2001/0031975 A1 10/2001 Whitman et al.
2002/0049454 A1 4/2002 Whitman et al.
2002/0165541 A1 11/2002 Whitman
2003/0038938 A1 2/2003 Jung et al.
2003/0165794 A1 9/2003 Matoba
2004/0111012 A1 6/2004 Whitman
2004/0133189 A1 7/2004 Sakurai
2004/0153124 A1 8/2004 Whitman
2004/0176751 A1 9/2004 Weitzner et al.
2004/0193146 A1 9/2004 Lee et al.
2005/0125027 A1 6/2005 Knodel et al.
2005/0131442 A1 6/2005 Yachia et al.
2006/0089533 A1 * 4/2006 Ziegler .............. A61B 1/00156
600/114
2006/0142656 A1 6/2006 Malackowski et al.
2006/0142740 A1 6/2006 Sherman et al.
2006/0142744 A1 6/2006 Boutoussov
2006/0259073 A1 11/2006 Miyamoto et al.
2006/0278680 A1 12/2006 Viola et al.
2006/0284730 A1 12/2006 Schmid et al.
2007/0005002 A1 1/2007 Millman et al.
2007/0023476 A1 2/2007 Whitman et al.
2007/0023477 A1 2/2007 Whitman et al.
2007/0029363 A1 2/2007 Popov
2007/0084897 A1 4/2007 Shelton, IV et al.
2007/0102472 A1 5/2007 Shelton, IV
2007/0152014 A1 7/2007 Gillum et al.
2007/0175947 A1 8/2007 Ortiz et al.
2007/0175949 A1 8/2007 Shelton, IV et al.
2007/0175950 A1 8/2007 Shelton, IV et al.
2007/0175951 A1 8/2007 Shelton, IV et al.
2007/0175955 A1 8/2007 Shelton, IV et al.
2007/0175961 A1 8/2007 Shelton, IV et al.
2007/0270784 A1 11/2007 Smith et al.
2008/0029570 A1 2/2008 Shelton, IV et al.
2008/0029573 A1 2/2008 Shelton, IV et al.
2008/0029574 A1 2/2008 Shelton, IV et al.
2008/0029575 A1 2/2008 Shelton, IV et al.
2008/0058801 A1 3/2008 Taylor et al.
2008/0109012 A1 5/2008 Falco et al.
2008/0110958 A1 5/2008 Mckenna et al.
2008/0147089 A1 6/2008 Loh et al.
2008/0167736 A1 7/2008 Swayze et al.
2008/0185419 A1 8/2008 Smith et al.
2008/0188841 A1 8/2008 Tomasello et al.
2008/0197167 A1 8/2008 Viola et al.
2008/0208195 A1 8/2008 Shores et al.
2008/0237296 A1 10/2008 Boudreaux et al.
2008/0251561 A1 10/2008 Eades et al.
2008/0255413 A1 10/2008 Zemlok et al.
2008/0255607 A1 10/2008 Zemlok
2008/0262654 A1 10/2008 Omori et al.
2008/0308603 A1 12/2008 Shelton et al.
2008/0308604 A1 * 12/2008 Timm .............. A61B 17/07207
227/180.1
2009/0012533 A1 1/2009 Barbagli et al.
2009/0090763 A1 4/2009 Zemlok et al.
2009/0099876 A1 4/2009 Whitman
2009/0138006 A1 5/2009 Bales et al.
2009/0171147 A1 7/2009 Lee et al.
2009/0182193 A1 7/2009 Whitman et al.
2009/0209990 A1 8/2009 Yates et al.
2009/0254094 A1 10/2009 Knapp et al.
2009/0289096 A1 * 11/2009 Shelton, IV ..... A61B 17/07207
227/180.1
2009/0299141 A1 12/2009 Downey et al.
2010/0001036 A1 * 1/2010 Marczyk .......... A61B 17/07207
227/175.1
2010/0001306 A1 1/2010 Park et al.
2010/0023022 A1 1/2010 Zeiner et al.
2010/0069942 A1 3/2010 Shelton, IV
2010/0179382 A1 * 7/2010 Shelton, IV ....... A61B 17/0644
600/104
2010/0193567 A1 * 8/2010 Scheib ............ A61B 17/07207
227/176.1
2010/0193568 A1 8/2010 Scheib et al.
2010/0211053 A1 8/2010 Ross et al.
2010/0225073 A1 9/2010 Porter et al.
2011/0071508 A1 3/2011 Duval et al.
2011/0077673 A1 3/2011 Grubac et al.
2011/0121049 A1 5/2011 Malinouskas et al.
2011/0125138 A1 5/2011 Malinouskas et al.
2011/0139851 A1 6/2011 Mccuen
2011/0155783 A1 6/2011 Rajappa et al.
2011/0155786 A1 6/2011 Shelton, IV
2011/0172648 A1 7/2011 Jeong
2011/0174099 A1 * 7/2011 Ross ...................... A61B 17/00
74/89.32
2011/0184245 A1 7/2011 Xia et al.
2011/0204119 A1 8/2011 Mccuen
2011/0218522 A1 9/2011 Whitman
2011/0276057 A1 11/2011 Conlon et al.
2011/0290851 A1 12/2011 Shelton, IV
2011/0290854 A1 12/2011 Timm et al.
2011/0295242 A1 12/2011 Spivey et al.
2011/0295269 A1 12/2011 Swensgard et al.
2011/0295270 A1 12/2011 Giordano et al.
2012/0000962 A1 1/2012 Racenet et al.
2012/0074199 A1 3/2012 Olson et al.
2012/0089131 A1 4/2012 Zemlok et al.
2012/0104071 A1 5/2012 Bryant
2012/0116368 A1 5/2012 Viola
2012/0143002 A1 6/2012 Aranyi et al.
2012/0172924 A1 7/2012 Allen, IV
2012/0205421 A1 8/2012 Shelton, IV
2012/0211542 A1 8/2012 Racenet
2012/0223121 A1 9/2012 Viola et al.
2012/0245428 A1 9/2012 Smith et al.
2012/0253329 A1 10/2012 Zemlok et al.
2012/0310220 A1 12/2012 Malkowski et al.
2012/0310221 A1 * 12/2012 Durant .................. A61B 34/30
606/1
2012/0323226 A1 12/2012 Chowaniec et al.
2012/0330285 A1 12/2012 Hartoumbekis et al.
2013/0018361 A1 1/2013 Bryant
2013/0093149 A1 4/2013 Saur et al.

(56) References Cited

U.S. PATENT DOCUMENTS

2013/0178838 A1 7/2013 Malkowski
2013/0181035 A1 7/2013 Milliman
2013/0184704 A1 7/2013 Beardsley et al.
2013/0214025 A1 8/2013 Zemlok et al.
2013/0274722 A1 10/2013 Kostrzewski et al.
2013/0277409 A1* 10/2013 Marczyk .............. A61B 17/068 227/175.1
2013/0282021 A1* 10/2013 Parihar .................. A61B 17/10 606/130
2013/0282052 A1 10/2013 Aranyi et al.
2013/0292451 A1 11/2013 Viola et al.
2013/0313304 A1 11/2013 Shelton, IV et al.
2013/0317486 A1 11/2013 Nicholas et al.
2013/0319706 A1 12/2013 Nicholas et al.
2013/0324978 A1 12/2013 Nicholas et al.
2013/0324979 A1 12/2013 Nicholas et al.
2013/0334281 A1 12/2013 Williams
2014/0005662 A1 1/2014 Shelton, IV
2014/0005678 A1* 1/2014 Shelton, IV ..... A61B 17/07207 606/130
2014/0012236 A1 1/2014 Williams et al.
2014/0012237 A1 1/2014 Pribanic et al.
2014/0012289 A1 1/2014 Snow et al.
2014/0025046 A1 1/2014 Williams et al.
2014/0110455 A1 4/2014 Ingmanson et al.
2014/0207125 A1 7/2014 Applegate et al.
2014/0207182 A1 7/2014 Zergiebel et al.
2014/0207185 A1 7/2014 Goble et al.
2014/0236173 A1* 8/2014 Scirica ............. A61B 17/00234 606/130
2014/0236174 A1 8/2014 Williams et al.
2014/0276932 A1 9/2014 Williams et al.
2014/0299647 A1* 10/2014 Scirica ............. A61B 17/07207 227/175.1
2014/0303668 A1* 10/2014 Nicholas .......... A61B 17/07207 606/207
2014/0358129 A1 12/2014 Zergiebel et al.
2014/0361068 A1 12/2014 Aranyi et al.
2014/0365235 A1 12/2014 Deboer et al.
2014/0373652 A1 12/2014 Zergiebel et al.
2015/0014392 A1 1/2015 Williams et al.
2015/0048144 A1 2/2015 Whitman
2015/0054753 A1* 2/2015 Morgan ............... A61B 17/072 345/173
2015/0076205 A1 3/2015 Zergiebel
2015/0080912 A1 3/2015 Sapre
2015/0105800 A1* 4/2015 Lohmeier .............. A61B 34/71 606/130
2015/0112381 A1 4/2015 Richard
2015/0122870 A1 5/2015 Zemlok et al.
2015/0133224 A1 5/2015 Whitman et al.
2015/0133957 A1 5/2015 Kostrzewski
2015/0136835 A1 5/2015 Shelton, IV et al.
2015/0150547 A1 6/2015 Ingmanson et al.
2015/0150574 A1 6/2015 Richard et al.
2015/0157320 A1 6/2015 Zergiebel et al.
2015/0157321 A1 6/2015 Zergiebel et al.
2015/0164502 A1 6/2015 Richard et al.
2015/0201931 A1 7/2015 Zergiebel et al.
2015/0272577 A1 10/2015 Zemlok et al.
2015/0282822 A1* 10/2015 Trees ................. A61B 18/1445 606/41
2015/0297199 A1 10/2015 Nicholas et al.
2015/0303996 A1 10/2015 Calderoni
2015/0320420 A1 11/2015 Penna et al.
2015/0327850 A1 11/2015 Kostrzewski
2015/0342601 A1 12/2015 Williams et al.
2015/0342603 A1 12/2015 Zergiebel et al.
2015/0374366 A1* 12/2015 Zergiebel ............. A61B 17/068 74/89.23
2015/0374370 A1 12/2015 Zergiebel et al.
2015/0374371 A1 12/2015 Richard et al.
2015/0374372 A1 12/2015 Zergiebel et al.
2015/0374449 A1 12/2015 Chowaniec et al.
2015/0380187 A1 12/2015 Zergiebel et al.
2016/0000513 A1* 1/2016 Shelton, IV ..... A61B 17/07207 606/1
2016/0095585 A1 4/2016 Zergiebel et al.
2016/0095596 A1 4/2016 Scirica et al.
2016/0106406 A1 4/2016 Cabrera et al.
2016/0113648 A1 4/2016 Zergiebel et al.
2016/0113649 A1 4/2016 Zergiebel et al.
2016/0174978 A1* 6/2016 Overmyer ........ A61B 17/07207 227/178.1
2016/0175060 A1 6/2016 Park
2016/0249918 A1* 9/2016 Shelton, IV ......... A61B 17/072 227/175.1
2016/0296216 A1 10/2016 Nicholas et al.
2016/0296234 A1* 10/2016 Richard ............. A61B 17/1155
2017/0211667 A1* 7/2017 Nicholas ................ A61B 34/71
2017/0281187 A1* 10/2017 Shelton, IV ....... A61B 17/3211
2017/0281188 A1* 10/2017 Shelton, IV ..... A61B 17/07207
2017/0281189 A1* 10/2017 Nalagatla ............. A61B 17/115
2017/0296173 A1 10/2017 Shelton, IV et al.
2017/0319200 A1* 11/2017 Nicholas .......... A61B 17/07207
2018/0049738 A1* 2/2018 Meloul ................ A61B 17/068
2018/0125594 A1* 5/2018 Beardsley ........ A61B 17/07207
2019/0069917 A1* 3/2019 Sholev ................... A61B 34/74
2024/0164775 A1* 5/2024 Nicholas .......... A61B 17/07207

FOREIGN PATENT DOCUMENTS

CN 102247182 A 11/2011
CN 104970884 A 10/2015
CN 107019537 A 8/2017
DE 102008053842 A1 5/2010
EP 0705571 A1 4/1996
EP 1769754 A1 4/2007
EP 1813212 A1 8/2007
EP 1980214 A2 10/2008
EP 2055243 A2 5/2009
EP 2100562 A2 9/2009
EP 2263568 A2 12/2010
EP 2316345 A1 5/2011
EP 2333509 A1 6/2011
EP 2649948 A1 10/2013
EP 2668910 A2 12/2013
EP 2937047 A1 10/2015
EP 3195812 A1 7/2017
ES 2333509 A1 2/2010
JP H0838488 A 2/1996
JP 2005125075 A 5/2005
KR 20120022521 A 3/2012
WO 2009039506 A1 3/2009
WO 2011108840 A2 9/2011
WO 2012040984 A1 4/2012

OTHER PUBLICATIONS

Chinese Office Action for application No. 2017103218172 dated Apr. 30, 2021 with English Translation.
Chinese Office Action for application No. 2021111861697 with English Translation.
Chinese Office Action issued in corresponding Chinese Application No. 202111186169.7 dated Aug. 31, 2023, 16 pages.
Chinese Office Action issued in corresponding Chinese Application No. 202111186169.7 dated Jan. 17, 2024, 10 pages.
Examination Report received for Australian Patent Application No. 2010241367, mailed on Aug. 20, 2015, 4 pages.
Examination Report received for Australian Patent Application No. 2014204542, mailed on Jan. 7, 2016, 3 pages.
Examination Report received for Australian Patent Application No. 2015200153, mailed on Dec. 11, 2015, 4 pages.
Extended European Search Report corresponding to counterpart Int'l Appln. No. EP 16164413.3 dated Dec. 8, 2016.
Extended European Search Report issued in European Application No. 17170006.5 dated Nov. 24, 2017.
Extended European Search Report received for European Patent Application No. 12197970.2, mailed on Jan. 28, 2016, 7 pages.
Extended European Search Report received for European Patent Application No. 14184882.0, mailed on May 12, 2015, 10 pages.

(56) References Cited

OTHER PUBLICATIONS

Extended European Search Report received for European Patent Application No. 14189358.6, mailed on Jul. 8, 2015, 5 pages.
Extended European Search Report received for European Patent Application No. 14196148.2, mailed on Apr. 23, 2015, 5 pages.
Extended European Search Report received for European Patent Application No. 14196704.2, mailed on Sep. 24, 2015, 11 pages.
Extended European Search Report received for European Patent Application No. 14197563.1, mailed on Aug. 5, 2015, 13 pages.
Extended European Search Report received for European Patent Application No. 14199783.3, mailed on Dec. 22, 2015, 14 pages.
Extended European Search Report received for European Patent Application No. 15151076.5, mailed on Apr. 22, 2015, 7 pages.
Extended European Search Report received for European Patent Application No. 15166899.3, mailed on Feb. 3, 2016, 9 pages.
Extended European Search Report received for European Patent Application No. 15167793.7, mailed on Apr. 5, 2016, 12 pages.
Extended European Search Report received for European Patent Application No. 15169962.6, mailed on Sep. 14, 2015, 7 pages.
Extended European Search Report received for European Patent Application No. 15173803.6, mailed on Nov. 24, 2015, 6 pages.
Extended European Search Report received for European Patent Application No. 15173804.4, mailed on Nov. 24, 2015, 6 pages.
Extended European Search Report received for European Patent Application No. 15173807.7, mailed on Nov. 24, 2015, 6 pages.
Extended European Search Report received for European Patent Application No. 15173910.9, mailed on Nov. 13, 2015, 6 pages.
Extended European Search Report received for European Patent Application No. 15184915.5, mailed on Jan. 5, 2016, 7 pages.
Extended European Search Report received for European Patent Application No. 15188539.9, mailed on Feb. 17, 2016, 9 pages.
Extended European Search Report received for European Patent Application No. 15190245.9, mailed on Jan. 28, 2016, 11 pages.
Extended European Search Report received for European Patent Application No. 15190760.7, mailed on Apr. 1, 2016, 7 pages.
International Search Report and Written Opinion received for PCT Application No. PCT/US2015/051837, mailed on Dec. 21, 2015, 10 pages.
Non-Final Office Action received for U.S. Appl. No. 18/407,343, mailed on Sep. 19, 2024, 9 pages.
Office Action received for Canadian Patent Application No. 2640399, mailed on May 7, 2015, 3 pages.
Office Action received for Chinese Patent Application No. 201210560638.1, mailed on Oct. 21, 2015, 17 pages.
Office Action received for Chinese Patent Application No. 201310125449.6, mailed on Feb. 3, 2016.
Office Action received for European Patent Application No. 14152236.7, mailed on Aug. 11, 2015, 5 pages.
Office Action received for European Patent Application No. 14159056.2, mailed on Oct. 26, 2015, 4 pages.
Office Action received for European patent Application No. 14184882.0, mailed on Apr. 25, 2016, 4 pages.
Office Action received for Japanese Patent Application No. 2011-084092, mailed on Jan. 14, 2016.
Office Action received for Japanese Patent Application No. 2011-084092, mailed on May 20, 2015.
Office Action received for Japanese Patent Application No. 2011-197365, mailed on Mar. 23, 2015.
Office Action received for Japanese Patent Application No. 2014-148482, mailed on Jun. 2, 2015.
Partial European Search Report received for European Patent Application No. 15190643.5, mailed on Feb. 26, 2016, 7 pages.
Partial European Search Report received for European Patent Application No. 14196704.2, mailed on May 11, 2015, 6 pages.
Partial European Search Report received for European Patent Application No. 14199783.3, mailed on Sep. 3, 2015, 6 pages.

* cited by examiner

FIG. 5
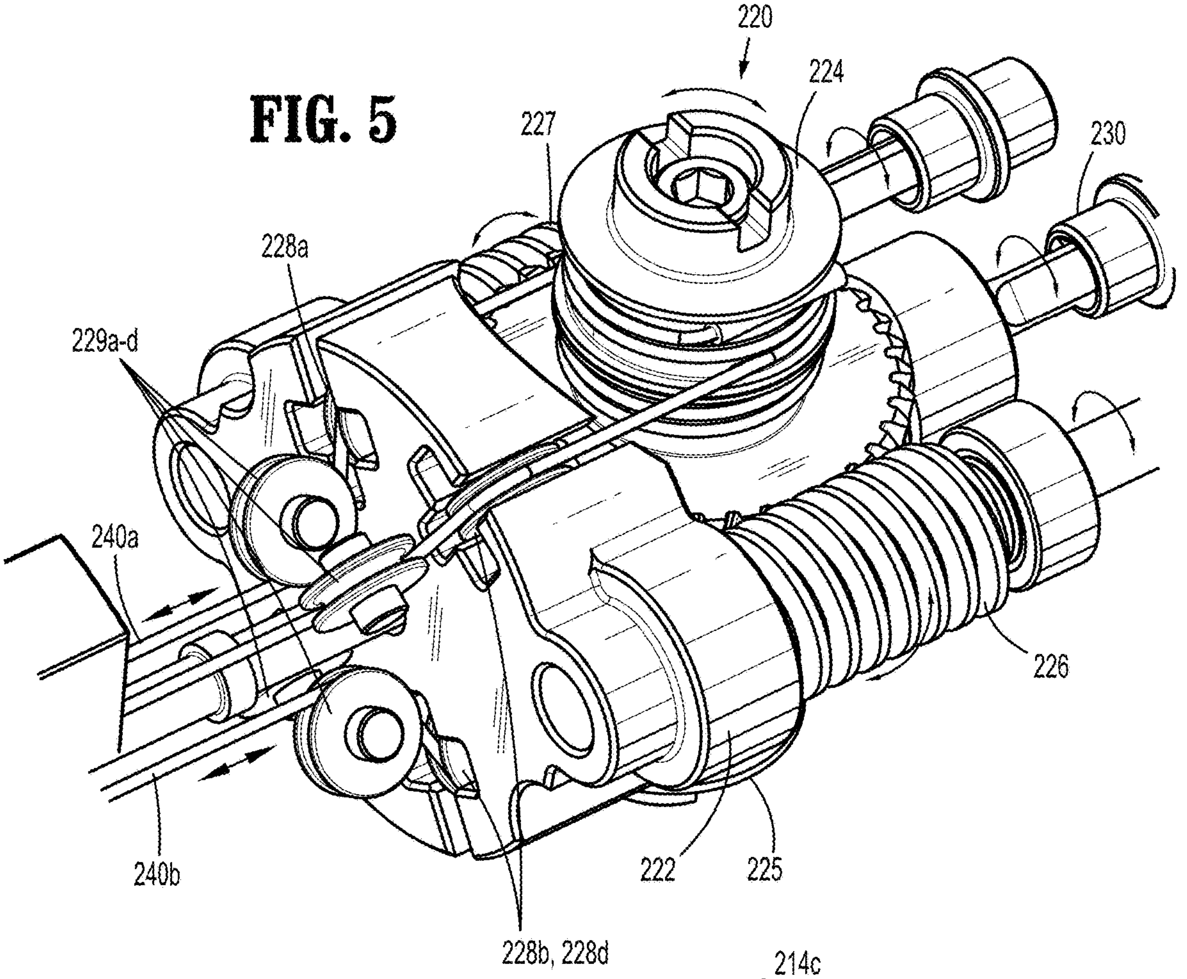
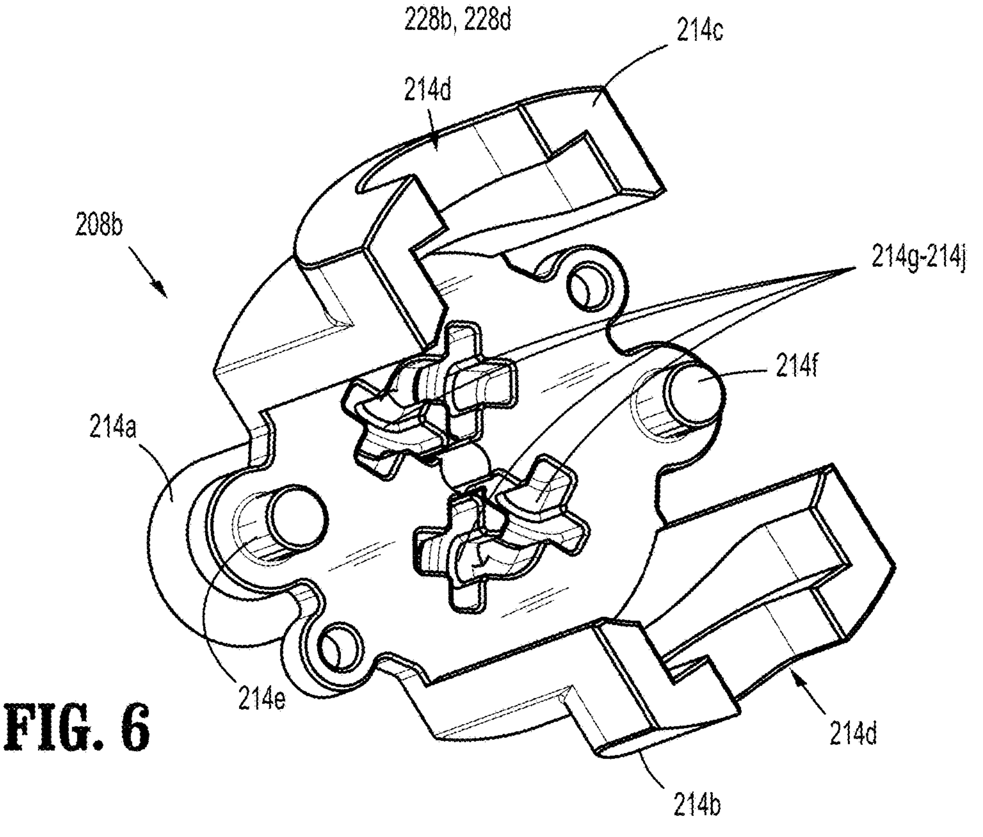
FIG. 6

SURGICAL SYSTEM INCLUDING ADAPTER ASSEMBLY WITH WORM GEAR ASSEMBLY

CROSS-REFERENCE TO RELATED APPLICATIONS

This application is a continuation of U.S. patent application Ser. No. 18/407,343, filed Jan. 8, 2024, which is a continuation of U.S. patent application Ser. No. 17/987,990, filed Nov. 16, 2022, now U.S. Pat. No. 11,864,763, which continuation of U.S. patent application Ser. No. 17/034,490, filed Sep. 28, 2020, now U.S. Pat. No. 11,504,123, which is a continuation of U.S. patent application Ser. No. 15/491,268, filed Apr. 19, 2017, now U.S. Pat. No. 10,799,239, which claims the benefit of U.S. Provisional Patent Application Ser. No. 62/333,584, filed May 9, 2016, the entire contents of each of which are incorporated by reference herein.

TECHNICAL FIELD

The present disclosure relates to adapter assemblies for use in surgical systems. More specifically, the present disclosure relates to adapter assemblies for use with, and to electrically and mechanically interconnect, electromechanical surgical devices and surgical end effectors, and to surgical systems including handheld electromechanical surgical devices and adapter assemblies for connecting surgical end effectors to the handheld electromechanical surgical devices.

BACKGROUND

A number of surgical device manufacturers have developed product lines with proprietary powered drive systems for operating and/or manipulating a surgical device. In many instances the surgical devices include a powered handle assembly, which is reusable, and a disposable end effector or the like that is selectively connected to the powered handle assembly prior to use and then disconnected from the end effector following use in order to be disposed of or in some instances, sterilized for re-use.

Many of the existing end effectors for use with many of the existing powered surgical devices and/or handle assemblies are driven by a linear force. For example, end effectors for performing endo-gastrointestinal anastomosis procedures, end-to-end anastomosis procedures and transverse anastomosis procedures, each typically require a linear driving force in order to be operated. These end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. Many of these adapter and/or adapter assemblies are complex devices including many parts and requiring extensive labor to assemble.

Adapter concepts often include a cable system for distal rotation and/or articulation. Some designs of cable systems include pulleys or lead screws with counter-directional threads to generate linear motion. Consistent with stroke dynamics, lead screw designs can require additional length to accommodate coordinated cable take-up and release. By comparison, pulley designs can be more compact than lead screw designs, but typically require different considerations including those associated with assembly and tensioning.

Accordingly, a need exists to develop adapters and/or adapter assemblies that incorporate fewer parts, are less labor intensive to assemble, and are ultimately more economical to manufacture. Specifically, a need exits to develop such adapters and/or adapter assemblies with improved pulley designs that simplify manufacturing and assembly as well as improve cable tensioning.

SUMMARY

According to an aspect of the present disclosure, an adapter assembly is provided. The adapter assembly selectively interconnects an end effector that is configured to perform a function and a surgical device that is configured to operate the end effector. The adapter assembly includes an outer tube having a distal end and a proximal end, a housing secured to the proximal end of the outer tube, and a cable drive assembly supported by the housing.

The cable drive assembly includes a worm gear, a cable gear coupled to the worm gear and rotatable in response to rotation of the worm gear, a capstan coupled to the cable gear and rotatable in response to rotation of the cable gear, and a cable coupled to the capstan. The cable may be axially translatable in response rotation of the capstan to actuate a function of the end effector while connected to the distal end of the outer tube.

In certain embodiments of the adapter assembly, the cable drive assembly may include a second worm gear, a second cable gear coupled to the second worm gear, a second capstan coupled to the second cable gear, and a second cable coupled to the second capstan. The second cable may be axially translatable in response to rotation of one or more of the second worm gear, the second cable gear, and the second capstan.

In some embodiments of the adapter assembly, the cable drive assembly may further include one or more pulleys supporting the cable and configured to direct the cable into the outer tube.

In certain embodiments of the adapter assembly, the cable drive assembly may further include a body portion that supports the worm gear and the cable gear in contacting relation with one another.

The adapter assembly may further include a firing assembly that extends through the cable drive assembly and into the outer tube. In some embodiments, the firing assembly may include a firing shaft that rotates independent of the cable drive assembly to actuate a firing function of the end effector.

The housing of the adapter assembly may include an outer housing and an inner housing that support the cable drive assembly therein.

In some embodiments of the adapter assembly, the outer tube defines a longitudinal axis that extends between the proximal and distal ends of the outer tube. The worm gear may be supported on a shaft member that extends in parallel relationship to the longitudinal axis of the outer tube. The shaft member may be rotatable to rotate the worm gear.

According to another aspect of the present disclosure, a surgical stapling apparatus is provided. The surgical stapling apparatus includes an end effector, a surgical device configured to operate the end effector, and an adapter assembly for selectively interconnecting the end effector and the surgical device.

The adapter assembly of the surgical stapling apparatus includes an outer tube having a distal end and a proximal end, a housing secured to the proximal end of the outer tube, and a cable drive assembly supported by the housing. The cable drive assembly includes a worm gear, a cable gear coupled to the worm gear, a capstan coupled to the cable gear, and a cable coupled to the capstan. The cable may be axially translatable in response rotation of one or more of the worm gear, the cable gear, and the capstan.

The adapter assembly of the surgical stapling apparatus may further include a firing assembly that extends through the cable drive assembly and into the outer tube. The firing assembly may include a firing shaft that rotates independent of the cable drive assembly to actuate a firing function of the end effector.

In some embodiments of the surgical stapling apparatus, the cable drive assembly may further include a second worm gear, a second cable gear coupled to the second worm gear, a second capstan coupled to the second cable gear, and a second cable coupled to the second capstan. The second cable may be axially translatable in response to rotation of one or more of the second worm gear, the second cable gear, and the second capstan.

In certain embodiments of the surgical stapling apparatus, the housing of the adapter assembly may include an outer housing and an inner housing. The inner and outer housings may support the cable drive assembly therein.

In some embodiments of the surgical stapling apparatus, the cable drive assembly may further include one or more pulleys supporting the cable and configured to direct the cable into the outer tube.

In certain embodiments of the surgical stapling apparatus, the cable drive assembly may further include a body portion that supports the worm gear and the cable gear in contacting relation with one another.

In some embodiments of the surgical stapling apparatus, the outer tube of the adapter assembly defines a longitudinal axis that extends between the proximal and distal ends of the outer tube. The worm gear may be supported on a shaft member that extends in parallel relationship to the longitudinal axis of the outer tube. The shaft member may be rotatable to rotate the worm gear.

According to yet another aspect of the present disclosure, an adapter assembly for selective connection to a surgical device is provided. The adapter assembly includes an outer tube having a distal end and a proximal end, a housing secured to the proximal end of the outer tube, and a cable drive assembly supported by the housing. The cable drive assembly includes a worm gear drive assembly, a cable gear assembly coupled to the worm gear drive assembly, and one or more cables coupled to the cable gear assembly and axially translatable within the outer tube.

In some embodiments, the cable drive assembly may further include a second worm gear, a second cable gear coupled to the second worm gear, a second capstan coupled to the second cable gear, and a second cable coupled to the second capstan.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 5 is an enlarged, perspective view, of the indicated area of detail shown in FIG. 4;

FIG. 6 is an enlarged, perspective view of a distal housing of the adapter assembly of FIG. 2;

DETAILED DESCRIPTION

Figure 1:
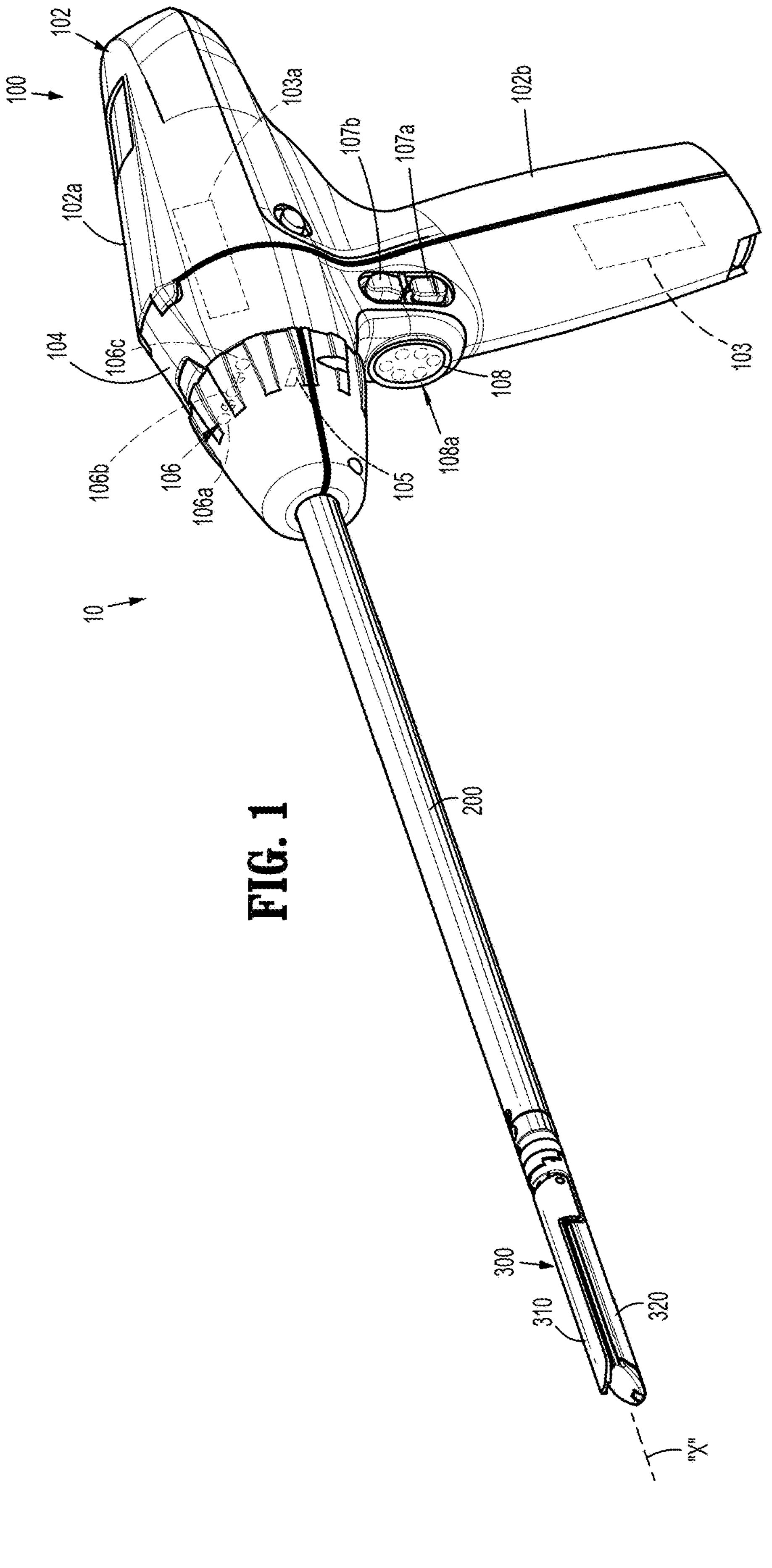
FIG. 1 is a perspective view of an electromechanical surgical system in accordance with the principles of the present disclosure.

Electromechanical surgical systems of the present disclosure include surgical devices in the form of powered handheld electromechanical instruments configured for selective attachment to a plurality of different end effectors that are each configured for actuation and manipulation by the powered handheld electromechanical surgical instrument. In particular, the presently described electromechanical surgical systems include adapter assemblies that interconnect the powered handheld electromechanical surgical instruments to the plurality of different end effectors. Each adapter assembly includes an articulation assembly and a firing assembly that is operatively coupled to a powered handheld electromechanical surgical instrument for effectuating actuation and/or manipulation of the plurality of different end effectors.

Embodiments of the presently disclosed electromechanical surgical systems, surgical devices/handle assemblies, adapter assemblies, and/or end effectors/loading units are described in detail with reference to the drawings, in which like reference numerals designate identical or corresponding elements in each of the several views. As used herein the term “distal” refers to that portion of the system, assembly, device, and/or component thereof, farther from the user, while the term “proximal” refers to that portion of the system, assembly, device, and/or component thereof, closer to the user.

Turning now to FIG. 1, an electromechanical surgical system, in accordance with the present disclosure, generally referred to as 10, includes a surgical device 100 in the form of a powered handheld electromechanical instrument, an adapter assembly 200, and a surgical loading unit (e.g., multiple- or single-use loading unit) or end effector 300. Surgical device 100 is configured for selective connection with adapter assembly 200, and, in turn, adapter assembly 200 is configured for selective connection with end effector 300. Together, surgical device 100 and adapter assembly 200 may cooperate to actuate end effector 300.

Surgical device 100 of electromechanical surgical system 10 includes a handle housing 102 including a controller or circuit board (not shown) and a drive mechanism 106 situated therein. The circuit board is configured to control the various operations of surgical device 100. Handle housing 102 defines a cavity therein (not shown) for selective removable receipt of a rechargeable battery 103 therein. The battery 103 is configured to supply power to any electrical components of surgical device 100. The drive mechanism 106 within the handle housing 102 is configured to drive rotatable shafts 106*a*-106*c* (and/or gear components—not shown) within handle housing 102 in order to perform the various operations of surgical device 100. In particular, drive mechanism 106 (and/or components thereof) is operable to selectively articulate end effector 300 about a longitudinal axis "X" and relative to a distal end of adapter assembly 200, to selectively rotate end effector 300 about longitudinal axis "X" and relative to handle housing 102, to selectively move/approximate/separate an anvil assembly 310 and a cartridge assembly 320 of end effector 300 relative to one another, and/or to fire a stapling and cutting cartridge within cartridge assembly 320 of end effector 300.

Handle housing 102 of surgical device 100 includes an upper housing portion 102*a* that houses various components of surgical device 100, and a lower hand grip portion 102*b* extending from upper housing portion 102*a*. Lower hand grip portion 102*b* of handle housing 102 may be disposed distally of a proximal-most end of upper housing portion 102*a* of handle housing 102. The location of lower hand grip portion 102*b* relative to upper housing portion 102*a* is selected to balance a weight of surgical device 100 while surgical device 100 is connected to or supports adapter assembly 200 and/or end effector 300.

A connection portion 104 of handle housing 102 is configured to secure to a proximal end of adapter assembly 200. Connection portion 104 houses an articulation contact surface 105 in electrical communication with the circuit board (not shown) of surgical device 100 to control drive mechanism 106. Each rotatable drive shaft 106*a*-106*c* of drive mechanism 106 can be independently, and/or dependently, actuatable and rotatable. In embodiments, rotatable drive shafts, 106*a*, 106*b*, and 106*c* may be arranged in a common plane or line with one another. As can be appreciated, any number of rotatable drive shafts can be arranged in any suitable configuration.

Handle housing 102 of surgical device 100 supports finger-actuated control buttons, rocker devices, and/or the like for activating various functions of surgical device 100. For example, handle housing 102 may support actuators including an actuation pad 108 in operative registration with sensors 108*a* that cooperate with actuation pad 108 to effectuate, for instance, opening, closing, and/or firing of end effector 300. Handle housing 102 can support actuators 107*a*, 107*b* which can be disposed in electrical communication with one or more motors (not shown) of drive mechanism 106 to effectuate rotation of rotatable drive shafts 106*a*, 106*b*, and/or 106*c* for actuation thereof to enable adjustment of one or more of the components of adapter assembly 200. Any of the presently described actuators can have any suitable configuration (e.g., button, knob, toggle, slide, etc.).

Reference may be made to International Application No. PCT/US2008/077249, filed Sep. 22, 2008 (Inter. Pub. No. WO 2009/039506), and U.S. Patent Application Publication No. 2011/0121049, filed on Nov. 20, 2009, the entire contents of each of which being incorporated herein by reference, for a detailed description of various internal components of and operation of exemplary electromechanical surgical systems, the components of which are combinable and/or interchangeable with one or more components of electromechanical surgical systems 10 described herein.

Figures 2A, 2B:
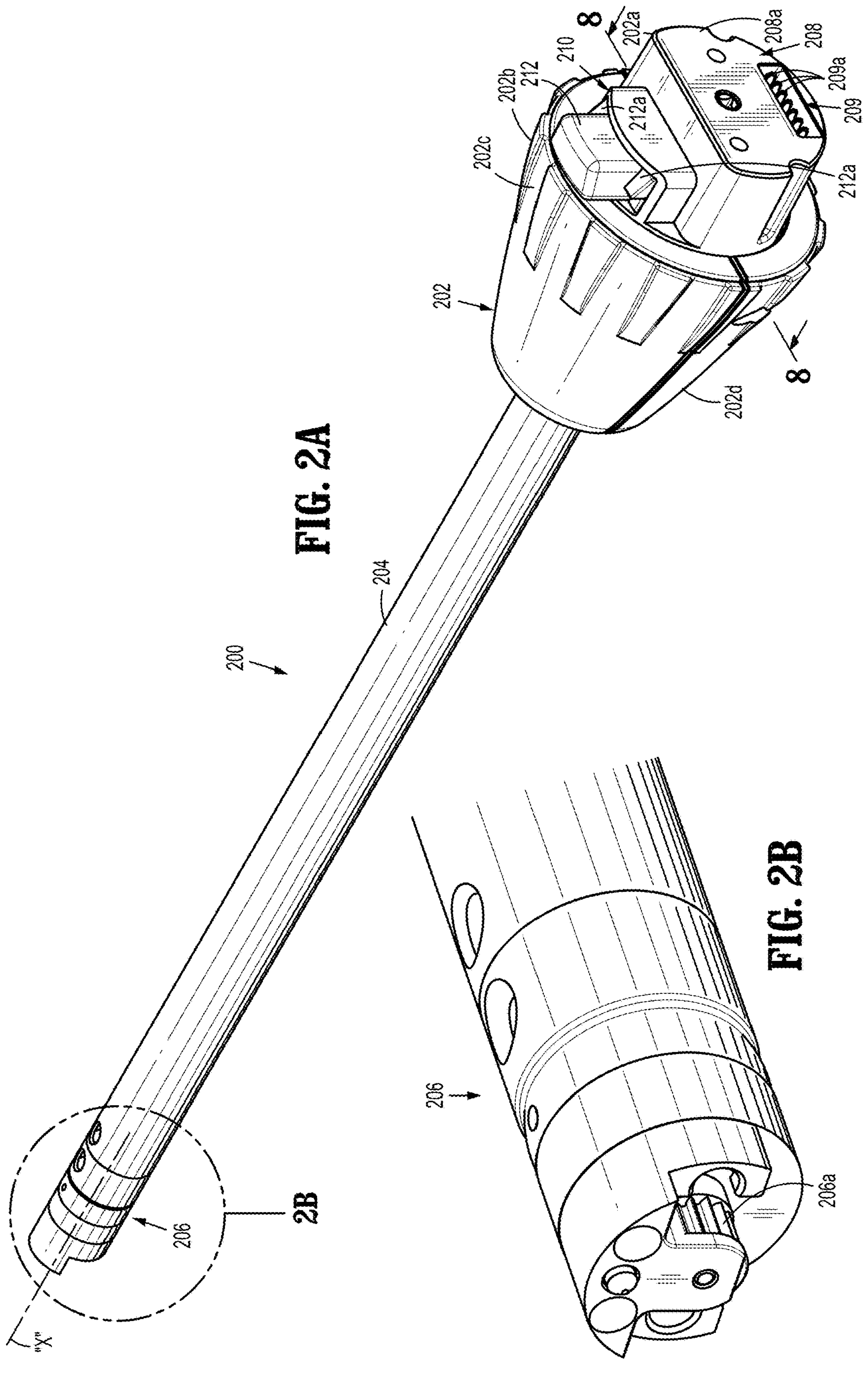
FIG. 2A is a perspective view of an adapter assembly of the electromechanical surgical system of FIG. 1.
FIG. 2B is a perspective view of the indicated area of detail shown in FIG. 2A.
Figure 3:
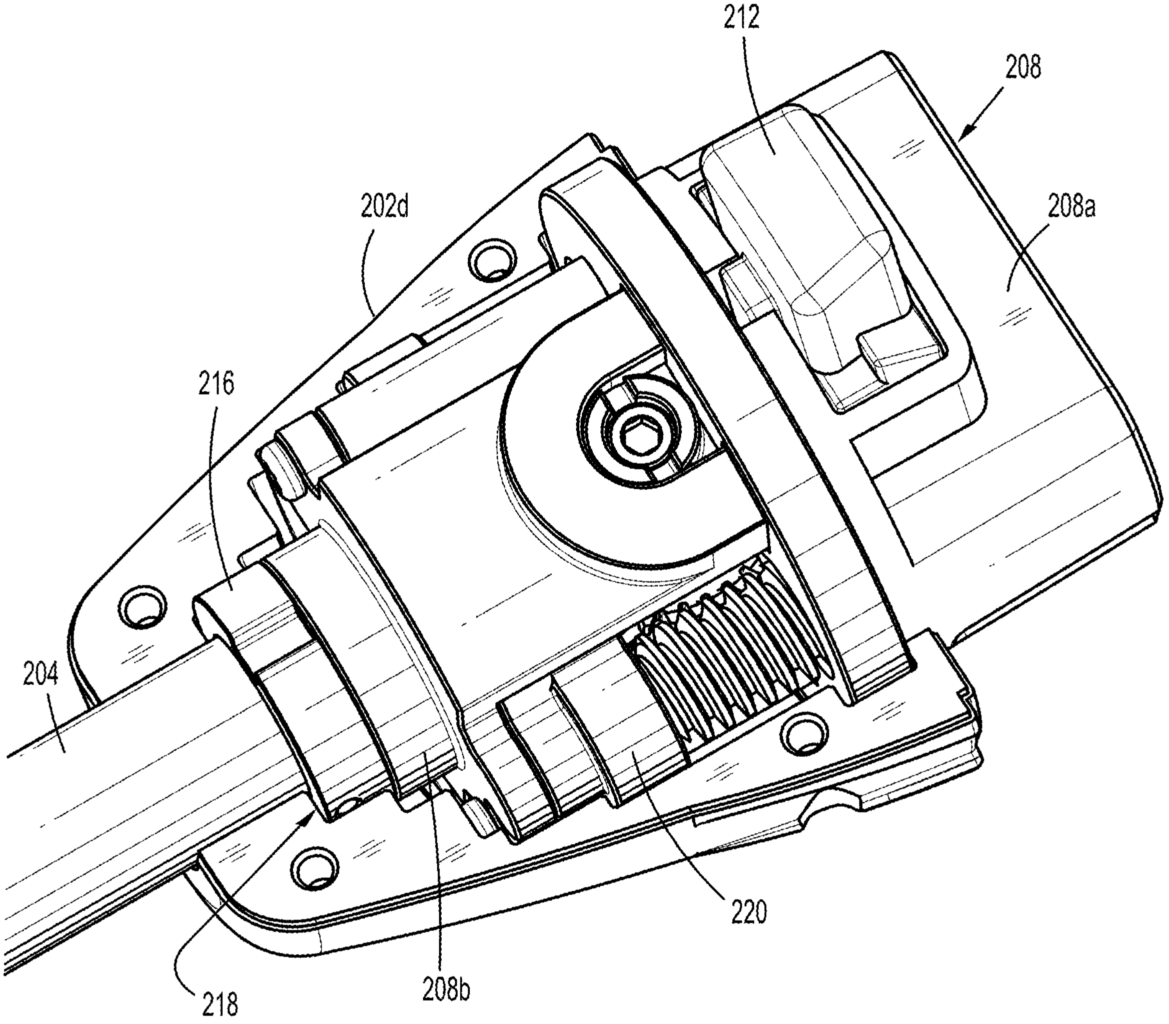
FIG. 3 is an enlarged, top, perspective view of a proximal portion of the adapter assembly of FIG. 2, the proximal portion of the adapter assembly shown with a portion of an outer housing thereof removed for clarity.
Figure 4:
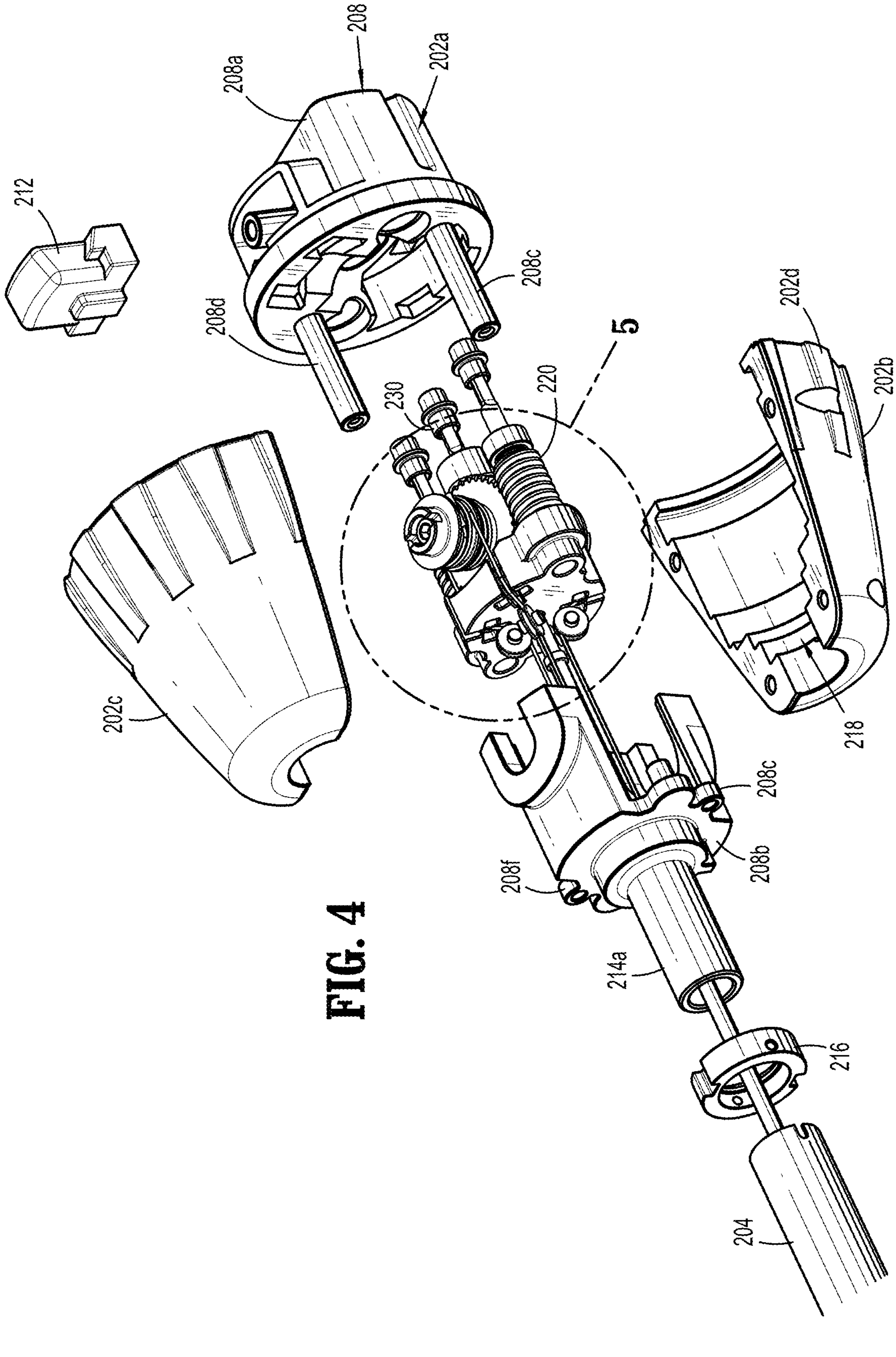
FIG. 4 is a perspective view, with parts separated, of the proximal portion of the adapter assembly of FIG. 2.

With reference to FIGS. 2A and 2B, adapter assembly 200 of electromechanical surgical system 10 includes a housing 202 at a proximal end portion thereof and an outer tube 204 that extends distally from housing 202 along longitudinal axis "X" to a distal end portion 206. Distal end portion 206 of outer tube 204 couples a distal end of adapter assembly 200 to a proximal end of end effector 300. Reference can be made to U.S. Patent Application Publication No. 2015/0297199, filed Apr. 21, 2014 for a detailed description of exemplary distal end portions, the entire contents of which are incorporated herein as discussed above. As described in U.S. Patent Application Publication No. 2015/0297199, the distal end portion may support a gimbal or the like that couple to an articulation assembly such as the articulation or cable drive assembly described herein to enable end effectors, such as end effector 300 of electromechanical surgical system 10, to articulate relative to adapter assembly 200 of electromechanical surgical system 10. Such distal end portions 206 may support a rotatable gear 206*a* that engages with a proximal end of end effector 300 to effectuate a firing thereof as described in greater detail below.

Referring to FIGS. 2A-4, housing 202 of adapter assembly 200 includes an inner housing 202*a* and an outer housing 202*b* having first and second housing halves 202*c*, 202*d*. Inner housing 202*a* includes a housing body 208 having a proximal housing body 208*a* and a distal housing body 208*b* that couple together via fastener-receiving arms 208*c*, 208*d* of proximal housing body 208*a* and fastener-receiving ears 208*e*, 208*f* of distal housing body 208*b*. Proximal housing body 208*a* of inner housing 202*a* supports an electrical assembly 209 therein and a mounting assembly 210 thereon.

Electrical assembly 209 of housing 202 may include a circuit board with contact pins 209*a* for electrical connection to a corresponding electrical plug (not shown) disposed in connection portion 104 of surgical device 100 (e.g., for calibration and communication of life-cycle information to the circuit board of the surgical device 100).

Mounting assembly 210 of housing 202 includes a mounting button 212 that is biased in an extended position and is configured to be depressed downwardly to a compressed position. In the compressed position, mounting button 212 is disposed in close approximation with housing body 208 of inner housing 202*a* and offset from the extended position thereof. Mounting button 212 includes sloped engagement features 212*a* that are configured to contact connection portion 104 (FIG. 1) of handle housing 102 while mounting button 212 is in the extended position to facilitate securement of housing 202 of adapter assembly 200 to connection portion 104 of handle housing 102. For a detailed description of similar electrical and mounting assemblies, reference can be made to U.S. Patent Application Publication No.

2015/0157320, filed Nov. 21, 2014 the entire contents of which are incorporated by reference herein.

Outer housing 202*b* of housing 202 is disposed around inner housing 202*a* of housing 202 to support an articulation or cable drive assembly 220 and a firing assembly 230 within housing 202 of adapter assembly 200. Distal housing body 208*b* of inner housing 208 includes a distal shaft 214*a* that is received within a proximal end of outer tube 204 and coupled thereto by a bearing 216 mounted within a channel 218 defined within outer housing 202*b* of housing 202.

As seen in FIG. 6, distal housing body 208*b* further includes mirrored arms 214*b*, 214*c* each defining a U-shaped passage 214*d*. U-shaped passages 214*d* of distal housing body 208*b* extend through arms 214*b*, 214*c* of distal housing body 208*b* and are configured to receive first and second cable gear assemblies 224, 225 of cable drive assembly 220 therein. Distal housing body 208*b* also includes pins or bosses 214*e*, 214*f* that extend proximally from a proximal surface of distal housing body 208*b*. The proximal surface of distal housing body 208*b* also defines distal pulley recesses 214*g*-214*j* therein.

With reference to FIGS. 5-7 and 10, cable drive assembly 220 includes a body portion 222, a first cable gear assembly 224, a second cable gear assembly 225, a first worm gear drive assembly 226, and a second worm gear drive assembly 227, proximal guide pulleys 228*a*-228*d*, and distal guide pulleys 229*a*-229*d*.

Body portion 222 of cable drive assembly 220 defines proximal pulley recesses 222*a*-222*d* that receive respective proximal guide pulleys 228*a*-228*d* therein to enable the respective proximal guide pulleys 228*a*-228*d* to rotate therein as cables 240*a*, 240*b* of cable drive assembly 220 rotate around respective proximal guide pulleys 228*a*-228*d* to manipulate end effector 300. Similarly, distal guide pulleys 229*a*-229*d* of cable drive assembly 220 are received within respective distal pulley recesses 214*g*-214*j* of distal housing body 208*b* of inner housing 202*a* to enable distal guide pulleys 229*a*-229*d* to rotate therein as cables 240*a*, 240*b* of cable drive assembly 220 rotate around respective distal guide pulleys 229*a*-229*d* to manipulate end effector 300.

Body portion 222 of cable drive assembly 220 includes an upper mounting projection 222*e* extending therefrom and positioned to partially receive first cable gear assembly 224 of cable drive assembly 220 therein for supporting first cable gear assembly 224 on upper mounting projection 222*e* of body portion 222. A lower mounting projection 222*f* (see FIG. 8) also extends from body portion 222 of cable drive assembly 220 in a direction opposite upper mounting projection 222*e* of body portion 222. Lower mounting projection 222*f* of body portion 222 is positioned to support second cable gear assembly 225 of cable drive assembly 220 thereon. Body portion 222 of cable drive assembly 220 further defines worm gear recesses 222*g*, 222*h* therein that rotatably receive first and second worm drive assemblies 226, 227, respectively in a proximal end thereof and pins 214*e*, 214*f* of distal housing body 208*b* in a distal end thereof. A firing shaft passage 222*i* is defined centrally through body portion 222 to receive a firing assembly 230 therein.

Figure 7:
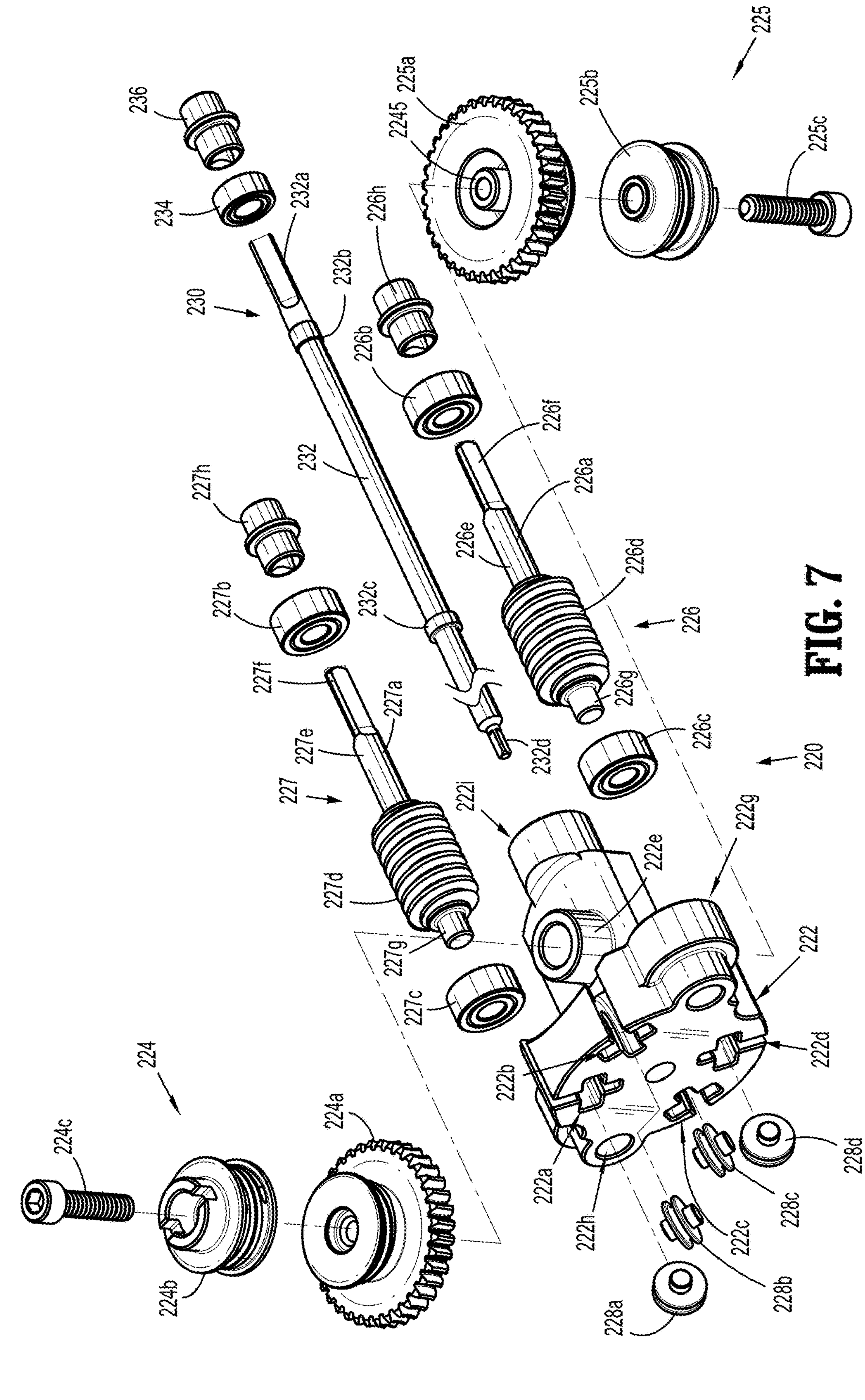
FIG. 7 is a perspective view, with parts separated, of a drive system of the adapter assembly of FIG. 2.
Figure 8:
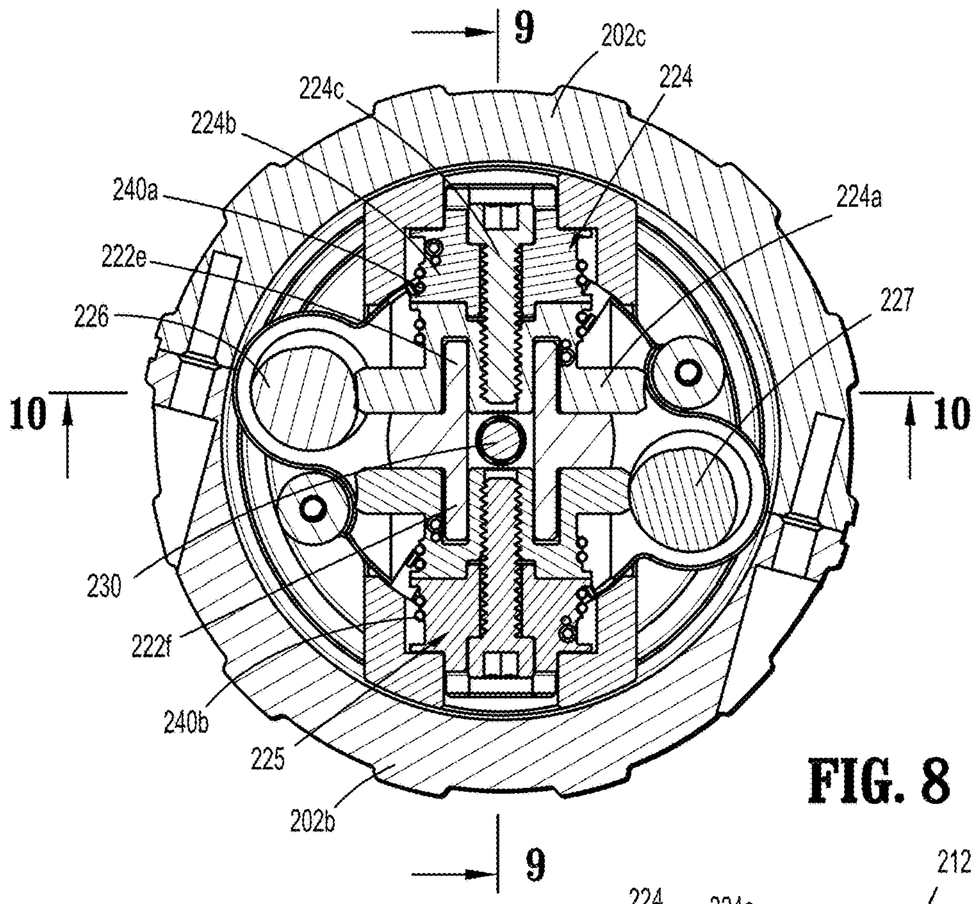
FIG. 8 is a cross-sectional view of the adapter assembly of FIG. 2 as taken along section line 8-8 shown in FIG. 2.

Referring to FIGS. 5, 7 and 8, first cable gear assembly 224 of cable drive assembly 220 includes an upper gear 224*a*, an upper capstan 224*b* supported on upper gear 224*a*, and an upper fastener 224*c* that couples upper capstan 224*b* to upper gear 224*a* while upper capstan 224*b* is coupled to upper mounting projection 222*e* of body portion 222 of cable drive assembly 220. Similarly, second cable gear assembly 225, which mirrors first cable gear assembly 224, includes a lower gear 225*a*, a lower capstan 225*b* supported on lower gear 225*a*, and a lower fastener 225*c* that couples lower capstan 225*b* to lower gear 225*a* while lower capstan 225*b* is coupled to lower mounting projection 222*f* of body portion 222 of cable drive assembly 220. Each of upper and lower gears 224*a*, 225*a* of respective first and second gear assemblies 224, 225 include a center protuberance 2245 that is received in respective upper and lower mounting projections 222*e*, 222*f* of body portion 222 to enable respective first and second gear assemblies 224, 225 to rotate about respective upper and lower mounting projections 222*e*, 222*f* of body portion 222. First and second driven members or cables 240*a*, 240*b* are wound around respective upper and lower capstans 224*b*, 225*b* and around respective proximal and distal guide pulleys 228*a*-228*d*, 229*a*-229*d* so that opposite ends/sides of each of the respective cables 240*a*, 240*b* extends distally through outer tube 204 to operatively couple to end effector 300 (e.g., to effectuate rotation and/or articulation thereof).

First worm gear drive assembly 226 of cable drive assembly 220 includes a first worm drive 226*a* rotatably supported between bearings 226*b*, 226*c*. First worm drive 226*a* includes a worm gear 226*d* secured on a shaft member 226*e*. Shaft member 226*e* has a proximal driving end 226*f* received in bearing 226*b* and a distal end 226*g* received in bearing 226*c*.

Similarly, second worm gear drive assembly 227 of cable drive assembly 220 includes a first worm drive 227*a* rotatably supported between bearings 227*b*, 227*c*. Second worm drive 227*a* includes a worm gear 227*d* secured on a shaft member 227*e*. Shaft member 227*e* has a proximal driving end 227*f* received in bearing 227*b* and a distal end 227*g* received in bearing 227*c*.

Figure 9:
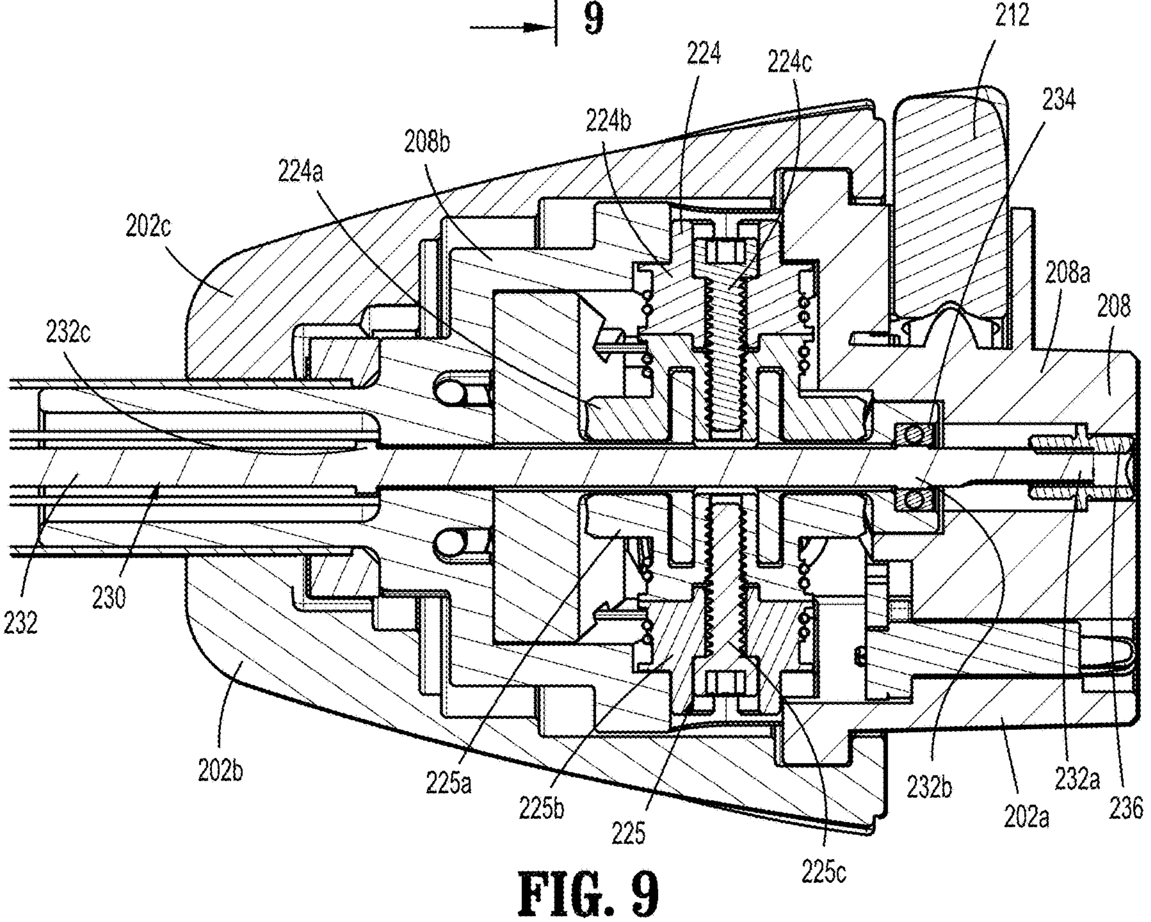
FIG. 9 is a cross-sectional view of a portion of the adapter assembly of FIG. 2 as taken along section line 9-9 shown in FIG. 8.
Figure 10:
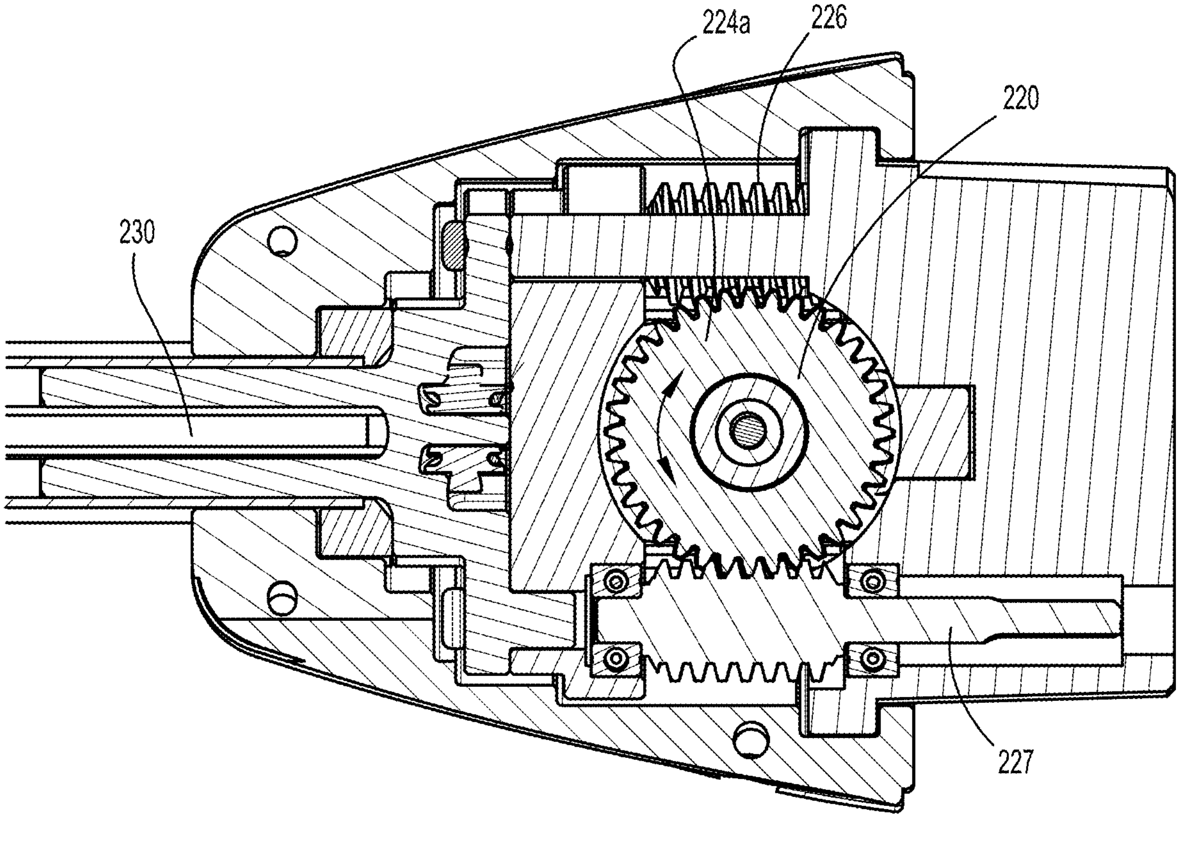
FIG. 10 is a cross-sectional view of a portion of the adapter assembly of FIG. 2 as taken along section line 10-10 shown in FIG. 8.

Referring to FIGS. 7, 9, and 10, firing assembly 230 of adapter assembly 200 includes a firing shaft 232, a bearing 234 supported on firing shaft 232, and an input socket 236 secured to a proximal end 232*a* of firing shaft 232. Firing shaft 232 of firing assembly 230 includes spaced collars 232*b*, 232*c* and a distal driving end 232*d*. Collar 232*b* of firing shaft 232 supports bearing 234 thereon and collar 232*c* of firing shaft 232 supports firing shaft 232 against distal housing body 208*b* of inner housing 202*a*. Distal driving end 232*d* of firing shaft 232 is extends to distal end portion 206 of outer tube 204 to effectuate a firing of end effector 300 as described in greater detail below.

Figure 11:
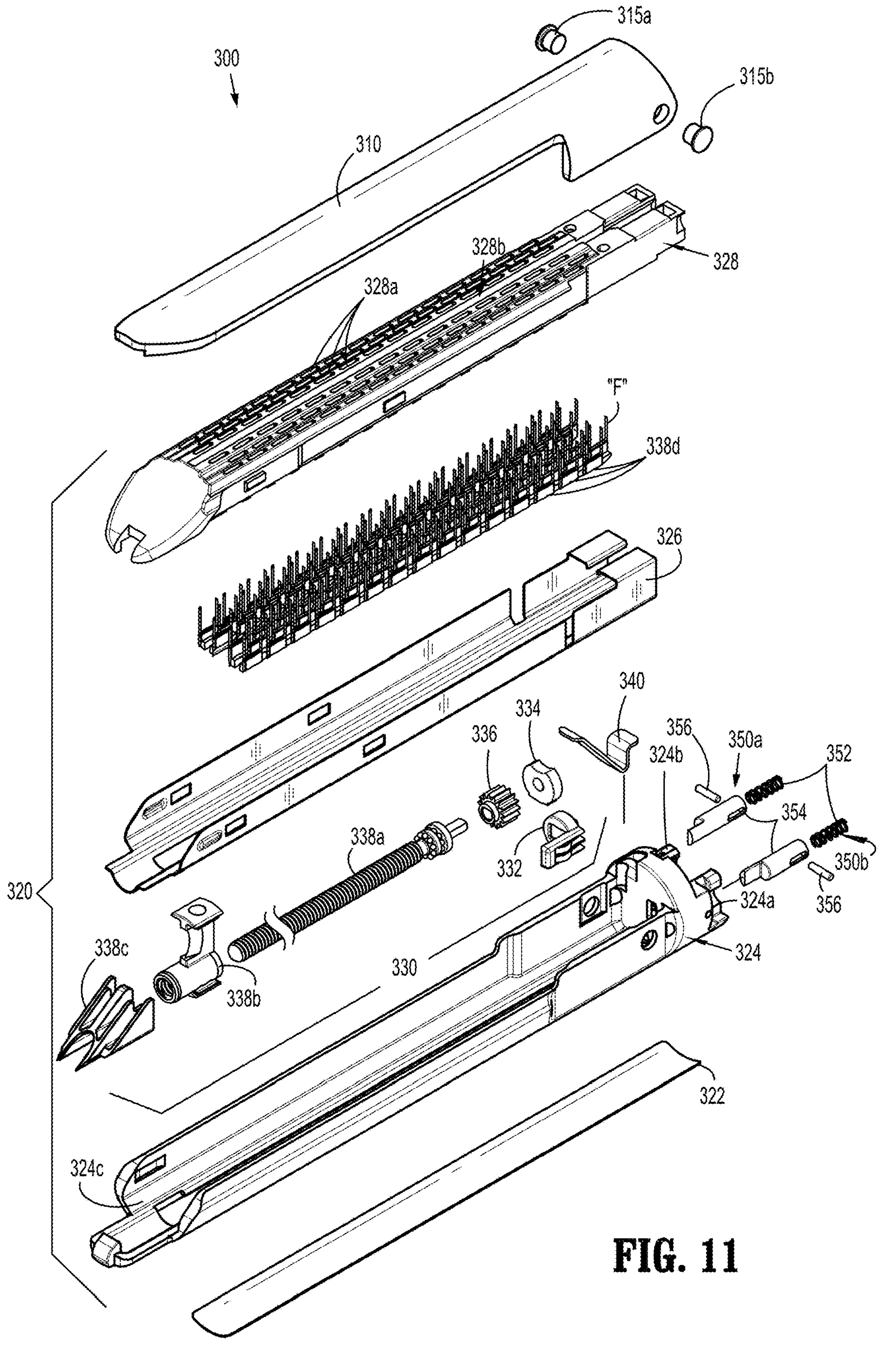
FIG. 11 is a perspective view, with parts separated, of an end effector of the electromechanical surgical system of FIG. 1.

Turning now to FIG. 11, an embodiment of an end effector 300 is shown. End effector 300 includes an anvil 310 and a cartridge assembly 320 that are pinned together by pins 315*a*, 315*b* and movable between open and closed conditions. Anvil 310 and cartridge assembly 320 cooperate to apply linear rows of fasteners "F" (e.g., staples). In certain embodiments, fasteners "F" are of various sizes, and, in certain embodiments, fasteners "F" are loaded into various lengths or rows of cartridge assembly 320 of end effector 300 (e.g., about 30, 45 and 60 mm in length).

Cartridge assembly 320 of end effector 300 includes a base 322 secured to a mounting portion 324, a frame portion 326, and a cartridge portion 328. Cartridge portion 328 has a tissue engaging surface that defines fastener retaining slots 328*a* and a knife slot 328*b* therein. Mounting portion 324 of cartridge assembly 320 has mating surfaces 324*a*, 324*b* on a proximal end thereof and defines a receiving channel 324*c* therein that supports frame portion 326, cartridge portion 328, and a fastener firing assembly 330 therein. Cartridge assembly 320 supports a biasing member 340 (e.g., a leaf spring) that engages anvil 310.

Fastener firing assembly 330 of end effector 300 includes an electrical contact member 332 for electrical communication with the circuit board of surgical device 100, a bearing member 334, a gear member 336 that engages rotatable gear 206*a* of adapter assembly 200, and a screw assembly 338. Screw assembly 338 of fastener firing assembly 330 includes a lead screw 338*a*, a drive beam 338*b*, and an actuation sled 338*c* that is engageable with pusher members 338*d*.

Cartridge assembly 320 of end effector 300 also supports plunger assemblies 350*a*, 350*b*. Each of plunger assemblies 350*a*, 350*b* includes a spring 352, a plunger 354, and a pin 356 that secures each plunger assembly to mounting portion 324 of cartridge assembly 320. Plunger assemblies 350*a*, 350*b* cooperate with the proximal end of cartridge portion 328 to facilitate securement of cartridge portion 328 within mounting portion 324.

In order to secure the proximal end of end effector 300 to distal end portion 206 of outer tube 204 of adapter assembly 200, the proximal end of end effector 300 is aligned with distal end portion 206 of adapter assembly 200 so that the proximal end of end effector 300 can be coupled to distal end portion 206 of adapter assembly 200 such that mating surfaces 324*a* and 324*b* of end effector 300 engage with distal end portion 206 of adapter assembly 200 and the teeth of gear member 336 of end effector 300 enmesh with the teeth of rotatable gear 206*a* of distal end portion 206 of adapter assembly 200.

In use, actuation pad 108 of surgical device 100 is actuated to rotate one or both of rotatable drive shafts 106*a*, 106*c* (e.g., clockwise and/or counterclockwise) of surgical device 100 via motors (not shown) disposed within surgical device 100.

Rotation of rotatable drive shaft 106*a* of surgical device 100 causes a corresponding rotation of worm gear 227*d* of worm drive assembly 227 and thus, rotation of lower gear 225*a* of gear assembly 225. Rotation of lower gear 225*a* of gear assembly 225 rotates lower capstan 225*b* of gear assembly 225 to draw/retract/tighten one side/end of cable 240*a* of cable drive assembly 220 while letting out/releasing the opposite side/end of cable 240*a*. Similarly, rotation of rotatable drive shaft 106*c* of surgical device 100 causes a corresponding rotation of worm gear 226*d* of worm drive assembly 226 and thus, rotation of upper gear 224*a* of gear assembly 226. Rotation of upper gear 224*a* of gear assembly 224 rotates upper capstan 224*b* of gear assembly 224 to draw/retract/tighten one side/end of cable 240*b* of cable drive assembly 220 while letting out/releasing the opposite side/end of cable 240*b*. Cables 240*a*, 240*b* of cable drive assembly 200 can be drawn/retracted/tightened and/or let out/released as desired to effectuate articulation (e.g., a pitch and/or a yaw) of end effector 300 about longitudinal axis "X" of adapter assembly 200.

To fire fasteners "F" from end effector 300, actuation pad 108 of surgical device 100 is actuated to rotate rotatable drive shaft 106*b* via a motor 103*a* (see FIG. 1) within handle housing 102, and to effectuate rotation of firing shaft 232 of firing assembly 230 about longitudinal axis "X" of adapter assembly 200. Rotation of firing shaft 232 of firing assembly 230 rotates rotatable gear 206*a* of distal end portion 206 of adapter assembly 200, which in turn, causes rotation of gear member 336 of end effector 300.

Rotation of gear member 336 of firing assembly 330 rotates lead screw 338*a* of firing assembly 330 and enables drive beam 338*b* of firing assembly 330 to axially advance along lead screw 338*a* and through longitudinal knife slot 328*b* of cartridge portion 328 by virtue of a threaded engagement between lead screw 338*a* and drive beam 338*b*. Drive beam 338*b* of firing assembly 330 engages anvil 310 of end effector 300 to maintain anvil 310 and cartridge assembly 320 of end effector 300 in approximation. Distal advancement of drive beam 338*b* of firing assembly 330 advances actuation sled 338*c* of firing assembly 330 into engagement with pusher members 338*d* of end effector 300 and fires the fasteners "F" from fastener retention slots 328*a* of cartridge portion 328 for forming against corresponding fastener forming pockets (not shown) defined within anvil 310. End effector 300 can be reset and cartridge portion 328 of cartridge assembly 320 can be replaced so that end effector 300 can then be re-fired as needed or desired.

Figure 12:
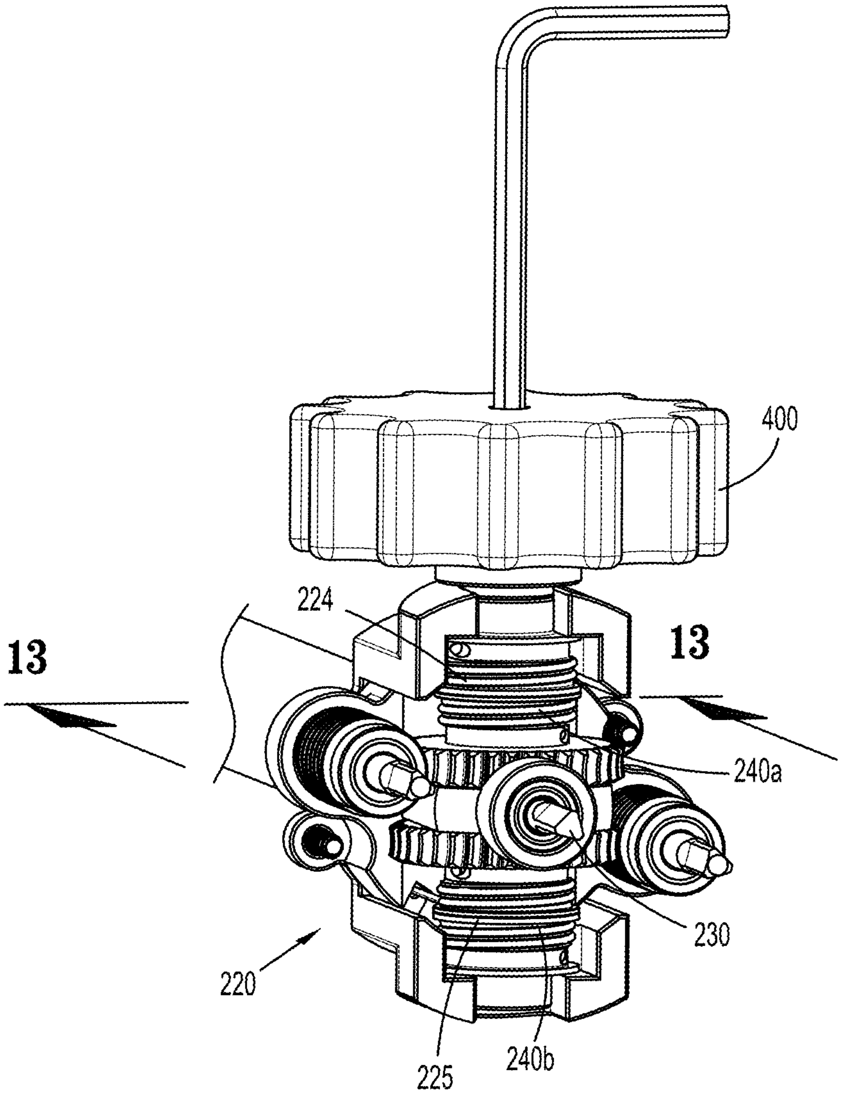
FIG. 12 is a perspective view illustrating cables of the drive system of FIG. 7 being tensioned with tensioning devices.
Figure 14:
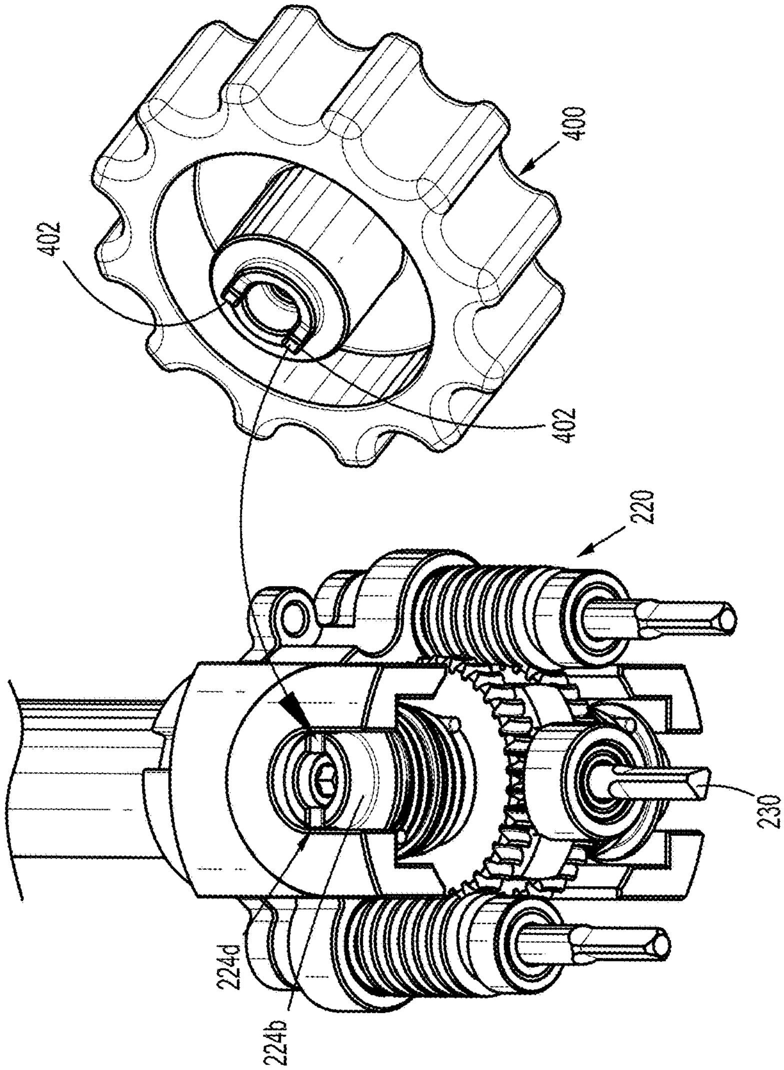
FIG. 14 is a perspective view of the drive system of FIG. 7 and of a tensioning device.
Figure 13:
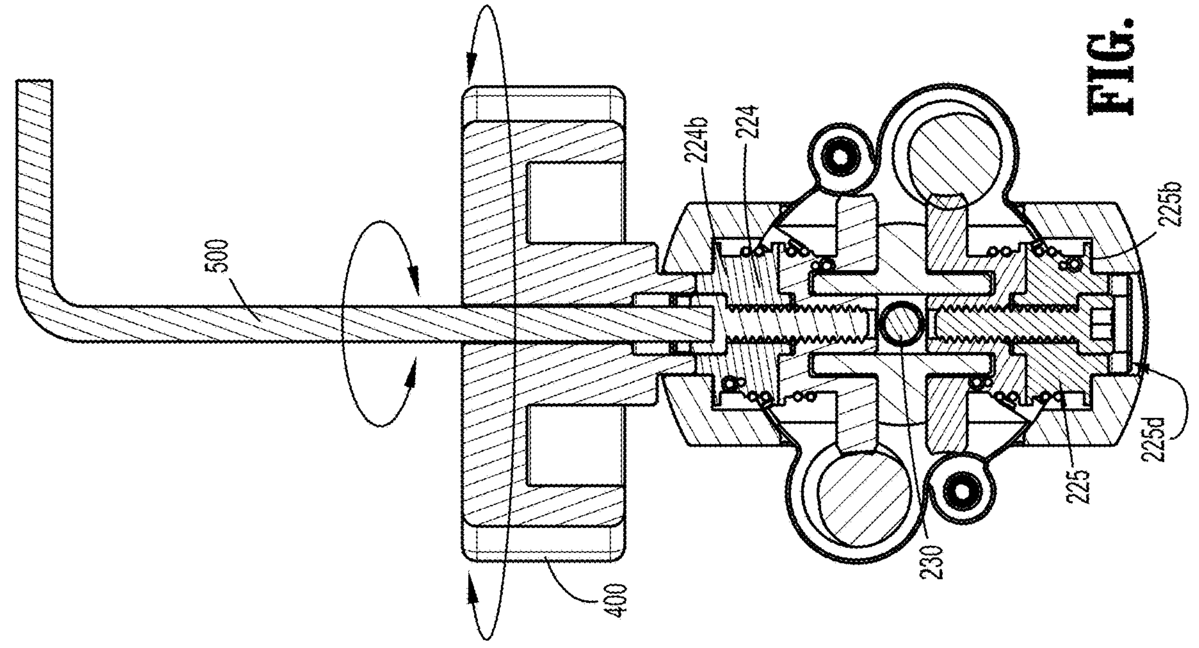
FIG. 13 is a cross-sectional view of FIG. 11 as taken along section line 13-13 shown in FIG. 12.

Turning now to FIGS. 12-14, upper capstan 224*b* of first cable gear assembly 224 defines a slot 224*d* therein and lower capstan 225*b* of second cable gear assembly 225 defines a slot 225*d* therein. Slots 224*d*, 225*d* of respective upper and lower capstans 224*b*, 225*b* are configured to selectively receive detents 402 of a rotatable knob 400 therein to enable tension in cables 240*a*, 240*b* to be adjusted upon rotation of upper and/or lower capstans 224*b*, 225*b* via rotation of rotatable knob 400. Rotatable knob 400 further defines a central channel 404 therethrough configured to selectively receive a fastener driver 500 (e.g., an Allen wrench) therethrough for tightening and/or loosening respective upper and lower fasteners 224*c*, 225*c* of respective first and second gear assemblies 224, 225 to further facilitate tension adjustments as needed or desired.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An adapter assembly for a surgical instrument, the adapter assembly comprising:
- an adapter housing;
- an outer tube extending distally from the adapter housing and configured to support an end effector; and
- a cable drive assembly supported by the adapter housing and including:
  - a worm gear;
  - a capstan; and
  - a first cable coupled to the capstan, the first cable axially translatable in response to rotation of the capstan and the worm gear to operate the end effector.

2. The adapter assembly of claim 1, further including a firing assembly that extends through the cable drive assembly and into the outer tube.

3. The adapter assembly of claim 2, wherein the firing assembly includes a firing shaft that rotates independently of the cable drive assembly to actuate a firing function of the end effector.

4. The adapter assembly of claim 1, wherein the cable drive assembly further includes a second capstan and a second cable coupled to the second capstan.

5. The adapter assembly of claim 4, wherein the second cable is axially translatable in response to rotation of a second worm gear.

6. The adapter assembly of claim 4, wherein the cable drive assembly further includes a first pulley supporting the first cable and a second pulley supporting the second cable.

7. The adapter assembly of claim 6, wherein the first pulley and the second pulley are configured to direct the respective first cable and second cable into the outer tube.

8. The adapter assembly of claim 1, wherein the adapter housing includes an outer housing and an inner housing, the inner and outer housings supporting the cable drive assembly therein.

9. The adapter assembly of claim 1, wherein the cable drive assembly further includes a body portion that supports the worm gear in contacting relation with a cable gear.

10. The adapter assembly of claim 1, wherein the outer tube defines a longitudinal axis that extends between proximal and distal ends of the outer tube, the worm gear supported on a shaft member that extends in parallel relationship to the longitudinal axis of the outer tube, the shaft member rotatable to rotate the worm gear.

11. An end effector assembly, comprising:
- an end effector;
- an adapter assembly for selectively connecting to the end effector, the adapter assembly comprising:
  - a proximal housing body;
  - a distal housing body coupled to the proximal housing body;
  - an outer tube extending distally from the distal housing body and supporting the end effector on a distal end portion of the outer tube; and
  - a cable drive assembly supported between the proximal and distal housing bodies and including:
    - a body portion;
    - a first cable gear assembly coupled to the body portion and supporting a first cable;
    - a second cable gear assembly coupled to the body portion and supporting a second cable; and
    - a plurality of guide pulleys supported between the body portion and the distal housing body, the plurality of guide pulleys configured to guide the first cable and the second cable through the distal housing body and into the outer tube for operating the end effector.

12. The end effector assembly of claim 11, wherein the cable drive assembly includes a first capstan supporting the first cable, and a second capstan supporting the second cable.

13. The end effector assembly of claim 12, further comprising a first gear that rotates the first capstan and a second gear that rotates the second capstan.

14. The end effector assembly of claim 13, wherein at least one of the first gear or the second gear is coupled to a worm gear.

15. A surgical stapling apparatus, comprising:
- an end effector;
- an adapter assembly for selectively connecting to the end effector, the adapter assembly including:
  - an adapter housing;
  - an outer tube extending distally from the adapter housing and supporting the end effector on a distal end portion of the outer tube; and
  - a drive assembly supported in the adapter housing and including:
    - at least one gear assembly; and
    - a worm gear assembly engaged with the at least one gear assembly to rotate the at least one gear assembly in the adapter housing as the worm gear assembly rotates in the adapter housing to articulate the end effector.

16. The surgical stapling apparatus of claim 15, further including a firing assembly that extends through the drive assembly and into the outer tube.

17. The surgical stapling apparatus of claim 16, wherein the firing assembly includes a firing shaft that rotates independent of the drive assembly to actuate a firing function of the end effector.

18. The surgical stapling apparatus of claim 15, wherein the drive assembly comprises a cable.

19. The surgical stapling apparatus of claim 18, further comprising at least one pulley supporting the cable and configured to direct the cable into the outer tube.

20. The surgical stapling apparatus of claim 15, wherein the adapter housing includes an outer housing and an inner housing, the inner and outer housings supporting the drive assembly therein.

* * * * *